(12) United States Patent
Chisholm et al.

(10) Patent No.: US 11,999,940 B2
(45) Date of Patent: *Jun. 4, 2024

(54) BALANCED SYSTEM AND METHOD FOR PRODUCTION OF MICROBIAL OUTPUT

(71) Applicant: Tenfold Technologies, LLC, Pilot Point, TX (US)

(72) Inventors: Robert Chisholm, McKinney, TX (US); Michael LaMontagne, Denton, TX (US); Robert N Ames, Pilot Point, TX (US); David P Lanciault, Plano, TX (US); John R Coyne, Bridgewater, CT (US)

(73) Assignee: TENFOLD TECHNOLOGIES, LLC, Pilot Point, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/844,544

(22) Filed: Mar. 15, 2013

(65) Prior Publication Data

US 2013/0324406 A1 Dec. 5, 2013

Related U.S. Application Data

(63) Continuation-in-part of application No. PCT/US2012/060010, filed on Oct. 12, 2012.
(Continued)

(51) Int. Cl.
*C12M 1/36* (2006.01)
*C05F 17/20* (2020.01)
(Continued)

(52) U.S. Cl.
CPC ............ *C12M 41/48* (2013.01); *C05F 17/20* (2020.01); *C05F 17/50* (2020.01); *C12M 21/04* (2013.01);
(Continued)

(58) Field of Classification Search
CPC ...... C12M 41/48; C12M 23/58; C12M 25/18; C12N 1/20; C12P 39/00; Y02P 20/145
See application file for complete search history.

(56) References Cited

U.S. PATENT DOCUMENTS 4,198,211 A * 4/1980 Shattock ................... C02F 3/28
165/163
4,279,753 A 7/1981 Nielson
(Continued)

FOREIGN PATENT DOCUMENTS

CA 2258254 A1 6/2000
CA 2292244 A1 * 6/2001
(Continued)

OTHER PUBLICATIONS

Ronald J Castle II & Julia Nemeth-Harn, Aerobic Vs. Anaerobic, Examining pretreatment of groundwater in small & rural systems, 2007, Water and Wastes Digest, accessed at https://www.wwdmag.com/aeration/aerobic-vs-anaerobic on Mar. 28, 2020 (Year: 2007).*
(Continued)

*Primary Examiner* — David W Berke-Schlessel
*Assistant Examiner* — Trent R Clarke
(74) *Attorney, Agent, or Firm* — Wilson Sonsini Goodrich & Rosati

(57) ABSTRACT

A system and method for the production of microbial consortiums and by-product material is provided. A physical containment system comprising phase spaces arranged in a discrete order to favor specific biological reactions is also provided. Phase profiles and phase data sets include the pre-determined physical and biological parameters for the phase space transitions. Movement of material from one phase to the next is hydraulically balanced enabling working fluid to continuously move in a fixed direction and rate of flow. Continuous monitoring of phase profiles and phase
(Continued)

data sets provide feedback to the system enabling alteration of the conditions in the system to control reactions therein.

14 Claims, 6 Drawing Sheets

Related U.S. Application Data

(60) Provisional application No. 61/581,679, filed on Dec. 30, 2011, provisional application No. 61/627,633, filed on Oct. 13, 2011.

(51) Int. Cl.

| | |
|---|---|
| *C05F 17/50* | (2020.01) |
| *C12M 1/00* | (2006.01) |
| *C12M 1/107* | (2006.01) |
| *C12M 1/12* | (2006.01) |
| *C12N 1/20* | (2006.01) |
| *C12P 3/00* | (2006.01) |
| *C12P 5/02* | (2006.01) |
| *C12P 7/40* | (2006.01) |
| *C12P 39/00* | (2006.01) |

(52) U.S. Cl.
CPC ............ *C12M 23/58* (2013.01); *C12M 25/18* (2013.01); *C12M 29/02* (2013.01); *C12M 47/06* (2013.01); *C12N 1/20* (2013.01); *C12P 3/00* (2013.01); *C12P 5/023* (2013.01); *C12P 7/40* (2013.01); *C12P 39/00* (2013.01); *Y02E 50/30* (2013.01); *Y02P 20/145* (2015.11); *Y02W 10/37* (2015.05); *Y02W 30/40* (2015.05)

(56) References Cited

U.S. PATENT DOCUMENTS

| | | | |
|---|---|---|---|
| 4,286,061 A | 8/1981 | Messing | |
| 4,318,993 A | 3/1982 | Ghosh et al. | |
| 4,696,746 A | 9/1987 | Ghosh | |
| 4,781,836 A | 11/1988 | Thiele et al. | |
| 5,059,066 A | 10/1991 | Schindler | |
| 5,232,596 A | 8/1993 | Castaldi | |
| 5,269,634 A | 12/1993 | Chynoweth | |
| 5,342,522 A | 8/1994 | Marsman | |
| 5,500,123 A | 3/1996 | Srivastava | |
| 5,525,229 A | 6/1996 | Shih | |
| 5,753,474 A | 5/1998 | Ramey | |
| 5,888,806 A | 3/1999 | Nguyen | |
| 6,342,378 B1 | 1/2002 | Zhang | |
| 6,569,332 B2 | 5/2003 | Ainsworth | |
| 6,582,596 B2 | 6/2003 | Mao | |
| 6,623,640 B2 | 9/2003 | Lanting | |
| 6,811,701 B2 | 11/2004 | Wilkie | |
| 6,908,555 B2 | 6/2005 | Arnett | |
| 6,946,073 B2 | 9/2005 | Daigger | |
| 7,001,519 B2 | 2/2006 | Linden | |
| 7,083,956 B2 | 8/2006 | Paterek | |
| 7,144,507 B2 | 12/2006 | Baskis | |
| 7,387,733 B2 | 6/2008 | Baskis | |
| 7,575,907 B1 | 8/2009 | Benemann | |
| 7,604,744 B2 | 10/2009 | Baskis | |
| 7,645,385 B2 | 1/2010 | Martin | |
| 7,713,413 B2 | 5/2010 | Barnes | |
| 7,713,417 B2 | 5/2010 | Sutton | |
| 7,966,741 B2 | 6/2011 | Gorbell | |
| 8,163,181 B2 | 4/2012 | Peters | |
| 2003/0166174 A1* | 9/2003 | Ono ........................ | C12P 13/04 435/106 |
| 2003/0173291 A1 | 9/2003 | Schimel | |
| 2004/0241790 A1* | 12/2004 | Eriksen .................... | A23J 1/005 435/41 |
| 2005/0035059 A1 | 2/2005 | Zhang | |
| 2009/0107913 A1 | 4/2009 | Johnson | |
| 2010/0032370 A1* | 2/2010 | Allen et al. .................... | 210/603 |
| 2010/0159539 A1 | 6/2010 | Ascon et al. | |
| 2010/0193433 A1 | 8/2010 | Hausin | |
| 2010/0201026 A1* | 8/2010 | Dvorak et al. ................ | 264/241 |
| 2010/0206791 A1 | 8/2010 | Lee | |
| 2010/0297740 A1 | 11/2010 | Li et al. | |
| 2011/0223644 A1 | 9/2011 | Kodukula et al. | |
| 2012/0156744 A1 | 6/2012 | Macdonald | |

FOREIGN PATENT DOCUMENTS

| | | | |
|---|---|---|---|
| CN | 2170946 Y | 7/1994 | |
| DE | 3248703 A1 | 7/1984 | |
| DE | 4000834 A1 | 8/1990 | |
| EP | 0555743 A1 | 2/1993 | |
| EP | 200878444 A1 | 11/1998 | |
| EP | 1818314 A2 | 8/2007 | |
| ES | 2006298 A6 | 4/1989 | |
| ES | 2090763 T3 | 10/1996 | |
| ES | 0878444 T3 | 1/1998 | |
| GB | 2276617 A | 10/1994 | |
| JP | 06-292560 A | 10/1994 | |
| JP | 7-507720 A | 8/1995 | |
| JP | 2006-256871 A | 9/2006 | |
| KR | 100948287 B1 | 4/2009 | |
| KR | 2010065551 A | 6/2010 | |
| WO | WO 94/21565 | 9/1994 | |
| WO | WO0073217 A1 | 12/2000 | |
| WO | 2003042117 A1 | 5/2003 | |
| WO | 2006108532 A1 | 10/2006 | |
| WO | 2007139264 A1 | 12/2007 | |
| WO | WO 2007-139264 A1 | 12/2007 | |
| WO | WO 2009103866 A2 * | 8/2009 | |
| WO | WO 2010014919 A1 * | 2/2010 | ............ C12M 21/04 |
| WO | WO-2010051622 A1 * | 5/2010 | ............ B01D 21/02 |
| WO | 2011017420 A2 | 2/2011 | |

OTHER PUBLICATIONS

Counterpart PCT Appln. No. PCT /US2012/060010, IPRP, dated Apr. 24, 2014.
Counterpart PCT Appln. No. PCT /US2012/060010, International Search Report, dated Mar. 31, 2014.
Counterpart PCT Appln. No. PCT /US2012/060010, Written Opinion, dated Mar. 31, 2014.
Cimrin et al. (2010) Phosphorous and Humic Acid Application Alleviate Salinity Stress of Pepper Seedling. African Journal of Biotechnology 9:5845-5851.
Leaungvutiviroj et al. (2010) Development of a New Biofertilizer with a High Capactiy for N2 Fixation, Phosphate and Potassium Solubilization and Auxin Production. Biosci. Biotechnol. Biochem 74:1098-1101.
Adesemoye et al. (2009) Plant-microbes Interactions in Enhanced Fertilizer-use Efficiency. Appl Microbial Biotechnol 85:1-12.
Quaggiotti et al. (2004) Effect of Low Molecular Size Humic Substances on Nitrate Uptake and Expression of Genes Involved in Nitrate Transport in Maize. Journal of Experimental Botany 55:803-813.
Szamrej et al. (2004) The Effect of Sex Steroids and Corticosteroids on the Content of Soluble Proteins, Nucleic Acids and Reducing Sugars in *Wolffia arrhiza* (L.) Wimm. (Lemnaceae). Polish Journal of Environmental Studies 13:565-571.
Glaser et al. (2002) Ameliorating Physical and Chemical Properties of Highly Weathered Soils in the Tropics with Charcoal—a Review. Biol Fertil Soils 35:219-230.
Sy et al. (2001) Methylotrophic Methylobacterium Bacteria Nodulate and Fix Nitrogen in Symbiosis with Legumes. Journal of Bacteriology 183:214-220.
Rohrig et al. (1996) Convergent Pathways for Lipochitooligosaccharide and Auxin Signaling in Tobacco Cells. Proc. Natl. Acad. Sci. USA 93:13389-13392.
Piccolo et al. (1992) Structural Characteristics of Humic Substances as Related to Nitrate Uptake and Growth Regulation in Plant Systems. Soil Biol. Biochem 24:373-380.

(56) References Cited

OTHER PUBLICATIONS

Shore et al. (1992) Effects of Estrone and 17β-estradiol on Vegetative Growth of Medicago Sativa. Physiologia Plantarum 84:217-222.
Jones et al. (1977) Effects of Steroidal Estrogens and Gibberellic Acid on Stem Elongation in Tall and Dwarf Cultivars of Pisum Sativum. New Phytol 79:493-499.
Costerton, Bill; Microbial ecology comes of age and joins the general ecology community; PNAS, Dec. 7, 2004, vol. 101. No. 49; pp. 16983-16984.
Querish, Nasib, et al.; Biofilm reactors for industrial bioconversion processes; employing potential of enhanced reaction rates; Microbial Cell Factories 2005, 4:24; Aug. 25, 2005; pp. 1-21.
European Patent Office supplementary search report on application 12839335.2 dated Apr. 29, 2015; 10 pages.
Pohland, F. G.; *Developments in Anaerobic Stabilization of Organic Wastes—The Two-Phase Concept*; Environmental Letters, 1(4), 1971; pp. 255-266.
Japanese Search Report for Application No. 2014-535935 dated Oct. 23, 2015.
JEFMA (Japan Environmental Facilities Manufacturers Association), No. 53, 2005.
Campanaro et al., "Metagenomic analysis and functional characterization of the biogas microbiome using high throughput shotgun sequencing and a novel binning strategy", Biotechnology for Biofuels; (2016) 9:26; 17 pages.
Chojnacka et al., "Noteworthy Facts about a Methane-Producing Microbial Community Processing Acidic Effluent from Sugar Beet Molasses Fermentation", Plos One, DOI:10.1371/journal.pone.0128008, May 22, 2015; 23 pages.
Guo et al., "Dissecting microbial community structure and methane-producing pathways of a full-scale anaerobic reactor digesting activated sludge from wastewater treatment by metagenomic sequencing", Microbial Cell Factories, (2015) 14:33; 11 pages.
Horz et al., "Methane-Oxidizing Bacteria in a California Upland Grassland Soil: Diversity and Response to Simulated Global Change", Dept. of Biological Sciences, Stanford University; Applied and Environmental Microbiology, vol. 71, No. 5, pp. 2642-2652, May 2015.
Kraus et al., "Taxonomic composition and gene content of a methane-producing microbial community isolated from a biogas reactor", Journal of Biotechnology; 136 (2008), pp. 91-101.
M.V. Kevbrina et al., "Growth of Mesophilic Methanotrophs at Low Temperatures", Experimental Articles, Microbiology, vol. 70, No. 4, (2001), pp. 444-451.
Pyzik et al., "Comparative analysis of deep sequenced methanogenic communities: identification of microorganisms responsible for methane production", Microbial Cell Factories, (2018) 17:197; 16 pages.
Whittenbury et al., "Enrichment, Isolation and Some Properties of Methane-utilizing Bacteria", Journal of General Microbiology (1970), vol. 61, No. 2; 17 pages.
Zakrzewski et al., "Profiling of the metabolically active community from a production-scale biogas plant by means of high-throughput metatranscriptome sequencing", Journal of Biotechnology, 158 (2012) pp. 248-258.
Zealand et al., "Microbial community composition and diversity in rice straw digestion bioreactors with and without dairy manure", Applied Microbiology and Biotechnology, (2018) 102:8599-8612.

\* cited by examiner

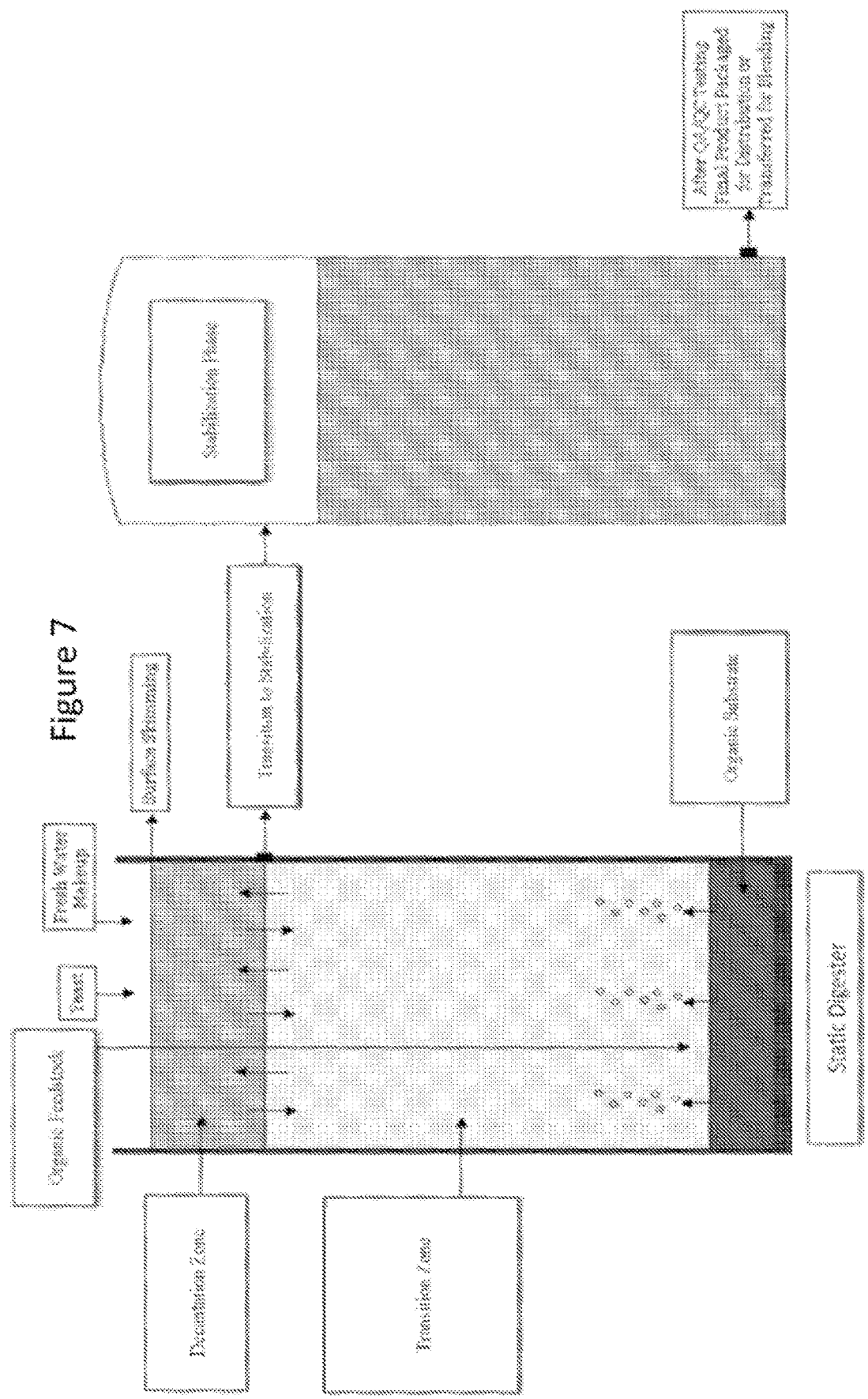

BALANCED SYSTEM AND METHOD FOR PRODUCTION OF MICROBIAL OUTPUT

FIELD OF THE DISCLOSURE

The field of the disclosure relates to microbial compositions. In particular, the field of the disclosure relates to a system and method for the production of a microbial output product.

BACKGROUND OF THE DISCLOSURE

The production of beneficial microbes and their by-products in various sequences and configurations is useful for multiple purposes including in agronomy. Among the various agronomy uses are soil conditioning for improved nutrient uptake; mineral solubilization; soil de-compaction; and remediation of various effluents and other soil and water contaminants. Beneficial microbes and their by-products may be processed, packaged, and added to soil enhancing products to be used with a variety of soil types, conditions, and environments to accomplish differing goals. Recently discovered bacterial isolates, pure strains of bacteria derived from mixed bacterial cultures, are capable of promoting plant growth. Microbial outputs can be used for remediation of contaminated soils such as those contaminated by petroleum hydrocarbons, benzene, and other industrial pollutants. These outputs support economic oil recovery (e.g., break up of paraffin in well heads); remediation of waste related to concentrated animal feeding operations (dairy, swine, poultry); and enhancement of composting.

A microbial consortium is a group of different species of microorganisms that act together as a community. Microbial consortia are found in biofilms such as found on trickling filters, and in various soil ecosystems. In a microbial consortium, the organisms work together in a complex system where all benefit from the activities of others in the community. In a microbial consortium, one might find any number of organisms with different metabolic capabilities. This could include organisms that are proteolytic (able to degrade proteins and amino acids); organisms that are saccharolytic (able to degrade various sugars); organisms that are lipolytic (able to digest lipids or fats); and organisms that are cellulytic (able to degrade cellulose or plant matter). In traditional anaerobic digester systems, these different metabolic capabilities allow the consortium to work together in degrading a variety of complex waste streams and creation of biofuels.

Traditionally, microbial consortia are viewed as more efficient at degrading complex organic wastes than single strains of organisms or even blended mixtures of microorganisms with a diversity of metabolic capabilities.

Two-phase systems have been found to enhance anaerobic conversion as proposed by Pohland and Ghosh, Environmental Letters, 1: 255-266 (1971). Various two or multi-phase systems have been disclosed (see, for example, U.S. Pat. Nos. 6,342,378, 7,083,956, 5,500,123, 5,525,229, 6,811,701, 4,696,746, 7,604,744, 7,144,507, 7,387,733, 7,144,507, 7,001,519, 6,946,073, 6,908,055, 5,342,522 and US Patent Pub. Nos. 20120156744, 20110223644, 20100193433, 20100159539). However, for the most part, these systems are directed to producing or maintaining biomass or producing biogas or biofuels. Furthermore, these systems have tended to be inefficient. The apparatus and methods of the disclosed embodiments are optimized for the production of microbial consortiums and their by-product material, as opposed to optimization of matter decomposition and gas production. Therefore, the system is designed as a matter of purpose not to produce significant amounts of methane gas or noxious by-products.

Microbial communities have been used to produce a material to stimulate plant growth. Examples are products sold by Advanced Microbial Solutions, LLC, CAMS) of Pilot Point, Texas under the trade names SuperBio® SoilBuilder™, SuperBio® AgBlend™, SuperBio® SoilLife™ and NutriLife. These products contain a community of microbes and biological material after a fermentation process. The AMS fermentation system produces a fermentation extract solution containing live microorganisms and bioactive compounds. The base fermentation extract solution is sold as SuperBio® SoilBuilder™, and serves as the primary ingredient for additional commercial products identified above. The fermentation extract solution contains many different species of microorganisms and many different bioactive compounds. The SoilBuilder™ product has generally been produced using a large batch fermentation system ("Legacy System") depicted in FIG. 7. The Legacy System involves the use of concurrent, overlapping, phases of fermentation. This batch bioreactor approach is less efficient than continuous production and resists optimization of productivity to meet growing demand volumes. One must adjust organic feed rate to ambient conditions. As a result, it is necessary to make expert, art-based decisions as to when and how to adjust for optimal performance. Since the system is an open system and exposed to environmental variables, ambient temperature, rainfall, sunlight can all greatly influence the process and there is limited flexibility to adapt the system to multiple products and uses.

SUMMARY

A balanced multi-phased bioreactor designed for the conversion of a plurality of organic materials into beneficial microbial based output is disclosed. The disclosed embodiments define a system and method for generation of beneficial microbial products derived from complex substrates. The system comprises a series of bioreactor spaces in a single vessel or multiple vessels representing discrete, optimized micro-environments. In each micro-environment, specific definable classes of organisms dominate. The embodiments further disclose a hydraulically balanced method of operation which supports creating defined consortiums of beneficial microbes. The method supports control of the environments to encourage growth of communities of highly diverse and interdependent microbial species. The result of this process is a microbial output comprising unique, balanced, and stable consortia of microorganisms and related by-products.

The multi-phased bioreactor comprises a physical containment system arranged as phase spaces. A phase space is a discrete isolated environment that favors specific biological reactions. The physical containment system arranges phase spaces in a discrete order to favor production of particular microbes in numerical dominance by genus and species of organism. The number of phases and types of microbes contained in the multi-phase bioreactor depends on the organic starting material and the desired microbial output.

The bioreactor's physical containment system supports continuous processing of a working fluid. Movement of material from one phase to the next is hydraulically balanced enabling the working fluid to continuously move in a prescribed direction and flow rate. The hydraulic balance is achieved by the input to the system being equal to the output.

This results in a system of manufacture and method for increasing production of biologically stable microbial consortium. The balanced multi-phase system of manufacture and methods used to create microbial output enables deployment of bioreactors in a variety of sizes and configurations to support a wide range of uses.

In a related aspect, is use of hydraulic shearing in the bioreactor. Shearing is accurately controlled throughout the process to add precision to the conditions in the bioreactor and its packed bed reactors. Controlled shearing is used to regulate growth of biofilm. The balanced and controlled hydraulic flow of material through the system, the configuration of a series of phases tailored to the desired output, and the phased transitions provide a better system of manufacturing of a microbial output comprising unique, balanced, and stable consortia of microorganisms and related by-products.

This system differs from traditional bioreactors and anaerobic digesters developed for specific industrial tasks such as wastewater degradation and bio-fuel production. Many of these traditional systems are optimized for decomposition of organic matter and production of biogas such as methane and hydrogen. This system provides for separation of hydrogenic, acidogenic, acetogenic and methanogenic phases of anaerobic activity in a bioreactor so that microbial population levels are optimized for each phase. Further, the phase space structure and phase profiles support introduction of other processes or reconfiguration of processes to support development of new outputs.

The phases in this system overlap. As one phase concludes, the next phase begins. Further, the phases can shift in time of occurrence in the physical containment system. In other embodiments, other phases can be present or one phase may be repeated, reflecting additional or different phases having different biology and nutrients present.

The multi-phased bioreactor recognizes the onset and conclusion of biological phases by analysis of phase profiles. Phase profiles and associated phase data sets provide effective controls to recognize phase onset, intra-phase changes, and phase conclusion. The multi-phased bioreactor supports alteration of biological phase occurrences in situ to optimize discrete optimized micro-environments. It provides a comprehensive mechanism to monitor and adapt a physical system to maintain and foster biological phases in an optimum productive environment supporting manufacture of a liquid combination of beneficial bacteria output stabilized as a product.

Further provided is the product, which may be a soil amendment or additive obtained from this process. This soil amendment or additive may be used in combination with fertilizer to modulate and particularly promote growth and/or increase biomass of a plant by applying an amount of said amendment to a substrate for growing said plant effective to modulate growth of said plant or plant part (e.g. root extension).

BRIEF DESCRIPTION OF THE DRAWINGS

FIG. 7 is a schematic diagram of the legacy system.

DETAILED DESCRIPTION

Figure 1:
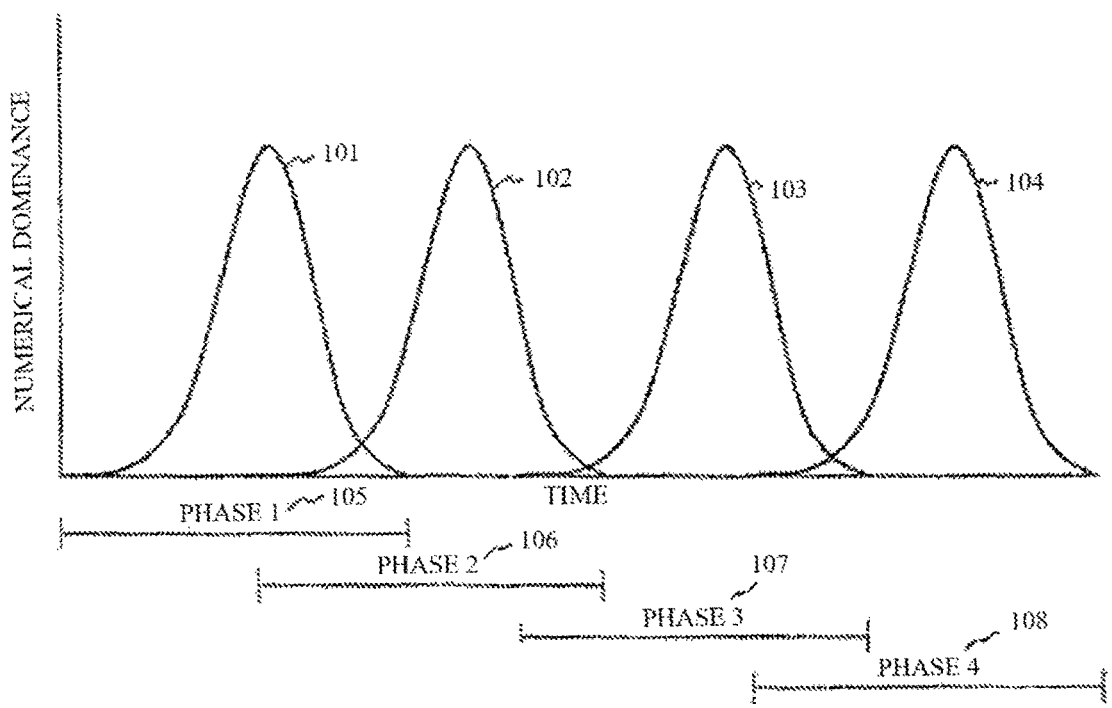
FIG. 1 is a graph of numerical dominance in phases.

While the compositions and methods heretofore are susceptible to various modifications and alternative forms, exemplary embodiments will herein be described in detail. It should be understood, however, that there is no intent to limit the invention to the particular forms disclosed, but on the contrary, the intention is to cover all modifications, equivalents, and alternatives falling within the spirit and scope of the invention as defined by the appended claims.

Definitions

The following terms are used in this disclosure:

"Bioreactor" is a physical containment system arranged in a discrete order to favor growth of particular microbes.

"Phase space" is a discrete isolated environment which favors specific biological reactions.

"Phase profile" is a predetermined set of physical, temporal, and biological parameters for a phase space.

"Phase data set" is a set of data correlated to a phase space and an associated phase profile.

"Organic load rate" is a rate at which organic feedstock is introduced into a physical system.

"Hydraulic load rate" is a rate at which water is introduced into a physical system.

"Internal recycle rate" is a rate at which a working fluid is recycled within a phase space.

"Hydraulic feed rate" is a rate at which working fluid is transferred between phase spaces.

"Hydraulic dwell time" is an amount of time that a working fluid is present in a phase space.

"Working fluid" is a fluid substance supporting and transporting biology and nutrients through the phase spaces.

DESCRIPTION OF SPECIFIC EMBODIMENTS

The embodiments provide a system and method for the creation of a microbial output and related by-products for use in agronomy.

Specifically provided is a multiphase method for processing organic material in less than 15 days, preferably in between about 5 to about 14 days and most preferably in about 7 days comprising:
  (a) a first phase wherein said organic material is hydrolyzed;
  (b) a second phase overlapping with said first phase wherein said hydrolyzed material of (a) is subject to acidogenesis and acetogenesis to obtain material comprising hydrogen, carbon dioxide, volatile organic acids and methanogenic precursors;
  (c) a third phase overlapping with said second phase wherein said methanogenic precursors in the material in (b) are converted to methane and said material in (b) is further subjected to denitrification and
  (d) a fourth phase overlapping with said third phase wherein said material from (c) is subject to stabilization and reversion.

The method may in one embodiment further comprise pasteurization and/or concentration of material from (d). In a particular embodiment and as will be set forth in further detail below, the material of (d) may be pasteurized and the pasteurized material may be concentrated.

The method in yet another embodiment and as will be set forth in further detail below, further comprises:
(a) receiving a set of profiles for each phase (hereinafter "phase profiles");
(b) monitoring a set of physical data from each phase which may include but is not limited to pH level, COD, conductivity and/or temperature;
(c) comparing the set of profiles from each phase to the set of physical data from each phase:
(d) deriving a control response to each phase based on the comparison of (c).
(e) applying the control response to each phase.

In yet another particular embodiment, organic material may be processed or microbial material may be produced by applying the organic material to a multiphase bioreactor or bioreactor system The multiphase bioreactor system may comprise:
(a) a first phase space for hydrolysis of organic material, which may be contained in a working fluid;
(b) a second phase space for acidogenesis/acetogenesis of organic material from the first phase space, wherein said second phase space overlaps with the first phase space of (a);
(c) a third phase space for methanogenesis of organic material from the second phase space, wherein said third phase space overlaps from the second phase space of (b);
(d) a fourth phase space for stabilization and reversion of the organic material of (c), and wherein said fourth phase space overlaps with the third phase space of (c).

In a particular embodiment,
(a) the first phase space recirculates working fluid comprising organic material at a first recycle rate through a first phase and a second phase in the first phase space, and passing the working fluid to the second phase space at a hydraulic feed rate;
(b) the second phase space recirculates working fluid at a second recycle rate through the second phase and a third phase in the second phase space, and passing the working fluid to the third phase space at the hydraulic feed rate;
(c) the third phase space recirculates working fluid at the second recycle rate through the second phase, the third phase, and a fourth phase, and passing the working fluid to the fourth phase space at the hydraulic feed rate and
(d) the fourth phase space recirculates working fluid at the second recycle rate through the third phase and the fourth phase, and passes the working fluid to an outlet port at the hydraulic feed rate.

The first recycle rate and/or second recycle rate may be proportional to the hydraulic feed rate. In particular, the first recycle rate proportional to the hydraulic feed rate is a first ratio in a range of 20 gallons per minute of the first recycle rate to 1 gallon per minute of the hydraulic feed rate to 40 gallons per minute of the first recycle rate to 1 gallon per minute of the hydraulic feed rate and/or the second recycle rate proportional to the hydraulic feed rate is a second ratio in a range of 25 gallons per minute of the second recycle rate to 1 gallon per minute of the hydraulic feed rate to 35 gallons per minute of the second recycle rate to 1 gallon per minute of the hydraulic feed rate.

Furthermore, in this bioreactor system, working fluid when introduced into the first phase space, sequentially passes through the first phase space, the second phase space, the third space, and the fourth phase space produces microbial output product at an outlet port. One or more phase spaces may be contained at least partially within a packed bed reactor, wherein said packed bed reactor comprises fixed media secured to the inside of said packed bed reactor.

In a particular embodiment,
(a) the first phase space comprises microorganisms having at least one of the metabolic functions selected from the group consisting of: methanogen, sulfur-reducing, dechlorination, iron-oxidation, nitrification and aromatic degrading and which may include but is not limited to at least one of *Syntrophus, Desulfovibrio, Symbiobacteria, Georgfuschia*, or *Nitrosomonas;*
(b) the second phase space comprises microorganisms having at least one of the metabolic functions selected from the group consisting of: methanogen, dechlorination, aromatic degrading, denitrifier, nitrification, anamox and high $CO_2$ and which may include but is not limited to at least one of *Syntrophus, Symbiobacteria, Georgfuschia, Thauera, Flavobacterium, Nitrosomonas, Owenweeksia*, or *Sphingomonas;*
(c) the third phase space comprises microorganisms having at least one of the metabolic functions selected from the group consisting of: aromatic degrading, denitrifier, nitrification, heterotroph, nitrification, methanotroph, and high $CO_2$ and which may include but is not limited to at least one of *Georgfuschia, Thauera, Flavobacterium, Nitrosomonas, Sedimini-bacterium, Methylonomas*, or *Sphingomonas* and
(d) the fourth phase space comprises microorganisms having at least one of the metabolic functions selected from the group consisting of: methanogen, aromatic degrading, denitrifier, nitrification, heterotroph, nitrification, anaerobe, sulfur-oxidation, anamox, high $CO_2$, and iron-oxidation and which may include but is not limited to *Syntrophus, Desulfovibrio, Symbiobacteria, Georgfuschia, Thauera, Nitrosomonas, Bellilinea, Sulfuritalea*, and *Owenweeksia*.

The multiphase bioreactor system may further comprise at least one of a pasteurizer, concentrator, a means for monitoring and/or detecting each phase space. In a particular embodiment, the multiphase reactor system wherein said system further comprises:
(a) a holding tank, connected to the first phase space, for mixing the working fluid and passing the working fluid to the first phase space;
(b) a pasteurizer connected to the fourth phase space; and
(c) a concentrator connected to the pasteurizer.

In a particular embodiment, organic material, when such organic material is organic feedstock, may be processed or microbial output may be produced by applying organic material and working fluid to the multiphase bioreactor system set forth above.

In a more particular embodiment, organic material and working fluid is applied to said multiphase system by
(a) providing an organic material, wherein said organic material is organic feedstock in a range of 0.001 to about 0.1 pound of organic feedstock per cubic foot of a total working capacity of the first phase space, the second phase space, the third phase space, and the fourth phase space as a first portion of the working fluid; and
(b) providing water in an amount proportional to the organic feedstock in a range of about 1 unit of the water per 2 units of the organic feedstock to about 1 unit of the water to 10 units of the organic feedstock as a second portion of the working fluid.

The method of may further comprise
(a) introducing a dry active yeast into the working fluid in the first phase space in an amount of about 0.2 to about 2 pound of the dry active yeast per 5000 gallons of the working fluid; and
(b) introducing a second working fluid into the working fluid in the first phase space in an amount range of one to five gallons, wherein steps (a) and (b) are performed a between about 38 to about 40 degrees C.

The method set forth above may further comprise comparing the set of profiles from each phase to the set of physical data from each phase. In a particular embodiment, the method comprises matching a final data set to a final phase profile of the microbial output and includes the steps of:
(a) matching a data pH level to a final pH level in a range of about 7.5 to 8.8;
(b) matching a data chemical oxygen demand level to a final chemical oxygen demand level in a range of about 90 mg/L to 120 mg/L; and
(c) matching a data conductivity level to a final conductivity level in a range of about 900 μS to 1200 μS.

Also provided is a multiphase bioreactor comprising a containment system which comprises:
(a) a holding tank for mixing working fluid;
(b) a complete mix reactor connected to the holding tank for recirculating working fluid;
(c) a clarifier connected to the complete mix reactor for separating solids from the working fluid;
(d) four or more packed bed reactors for hydrolysis, acidogenesis, acetogenesis, methanogenesis, stabilization and reconstitution of organic material, wherein each packed bed reactor comprises fixed media, wherein each packed bed reactor is in fluid communication with at least the adjacent packed bed reactor and wherein the clarifier connected to the complete mix reactor is in fluid communication with a first packed bed reactor, a packed bed reactor adjacent to said complete mix reactor coupled with a clarifier, wherein fixed media is secured to the inside of each packed reactor and
(e) a container for deposition of the processed organic material from said reactors and operatively connected to a final packed bed reactor, a packed bed reactor which is at least a fourth packed bed reactor.

In a particular embodiment, the complete mix reactor, clarified and packed bed reactors are formed in a continuous uninterrupted tube. In another embodiment, the bioreactor further comprises a pasteurizer connected to a final packed bed reactor. In yet another embodiment, the bioreactor further comprises a concentrator connected to said pasteurizer and having an outlet to said container for the deposition of process organic material. The multiphase bioreactor may additionally comprise:
(a) a set of system controls operatively coupled to the containment system;
(b) a set of system sensors operatively coupled to the containment system;
(c) a set of phase data set, derived from the set of system sensors and
(d) a set of phase profiles.

As noted above, further provided is a method for producing microbial output from an organic material comprising applying organic material and working fluid to the bioreactor set forth above under conditions sufficient to produce said microbial output in less than about 15 days.

Also provided is a soil additive or amendment produced using the methods set forth above and using the systems and bioreactor set forth above. Such a soil amendment may have the following characteristics:
(a) has a pH of about 7.5 to 8;
(b) COD range less than about 150 mg/L;
(c) Conductivity range of about 600 uS to 1400 uS;
(d) Color clear amber between about 500 pt/co units to about 700 pt/co units in a platinum to cobalt (pt/co) scale;
(e) comprises at least one of *Syntrophus, Desulfovibrio, Symbiobacteria, Georgfuschia, Thauera, Nitrosomonas, Bellilinea, Sulfuritalea,* and *Owenweeksia;*
(f) has a biomass greater than $10^7$ cells ml$^{-1}$;
(g) contains between about 10-60 ng/ml DNA;
(h) comprises at least eight microbial species or is a filter sterilized broth or cell fraction derived therefrom.

In a specific embodiment, the soil amendment further comprises at least 20 microbial species appearing no more than one time.

Bioreactor Phase Spaces

A physical containment system is provided in which a working fluid flows. The working fluid flows in the system at a rate of approximately one gallon per minute. The working fluid supports a number of competitive microbial species which are nourished by nutrients in the working fluid. The physical containment system arranges phase spaces in a discrete order to create a multi-phase bioreactor. The order is based on pre- and post-conditions that facilitate the processing of organic material. The phase spaces are provided with pre-determined, controlled and favorable environments in which the biological communities react in a predictable and planned manner. The physical containment system allows for adjusting the environments in real-time. This embodiment describes the end-to-end creation of the microbial output. Multiple phase spaces may be in use at the same time supporting creation of a variety of microbial outputs.

Bioreactor Phases

The process used in this embodiment comprises four sequential phases. FIG. 1 provides a graph of a four phased implementation of this embodiment. First phase 105, represented by curve 101, comprises a hydrolysis phase. Second phase 106, represented by curve 102, comprises an acidogenesis and acetogenesis phase. Third phase 107, represented by curve 103, comprises a methanogenesis phase. Fourth phase 108, represented by curve 104, comprises a reversion/stabilization phase. In each phase, the numerical dominance of one biological consortium is favored over other biological consortia present. One feature of this embodiment is the overlap of phases. As one phase concludes, the next phase begins. Further, the phases can shift in time of occurrence in the physical containment system. In other embodiments, other phases can be present or one phase may be repeated, reflecting additional or different phases having different biology and nutrients present.

In the hydrolysis phase, organic matter decomposes through mechanical, biological, and/or chemical means into slurry of uniform size and solubility. Chemically, polymers are hydrolyzed into oligomers or monomers. In the acidogenesis phase, soluble organics created in the hydrolysis phase are converted into short-chain organic acids. Oligomers or monomers are metabolized by fermentative bacteria to produce hydrogen, carbon dioxide, and volatile organic acids such as acetic acid, propionic acid, and butyric acid. In the acetogenesis phase, volatile organic acids are converted to methanogenic precursors (hydrogen, carbon dioxide, and acetate) by strophic acetones. In the methanogenesis phase, methane is produced from acetate, or from hydrogen and carbon dioxide.

Fourth phase 108 achieves stabilization. Process management refines the material in fourth phase 108 to meet a predetermined standard of colloidal clarity, presenting a phase profile of desirable and repeatable attributes. The microbial output product of fourth phase 108 will have a consortium of microbes and their by-products produced through the reaction process. The microbial output product may be further processed in external systems.

Phase Profiles

Each phase space is characterized by a set of physical, chemical, biological, and temporal parameters known as a phase profile. Each phase profile is predetermined and forms a portrait of the phase and its onset and completion. The physical containment system periodically registers and records each parameter in each phase space to create a phase data set. The phase data set provides input to control systems that perform a plurality of functions to assure the predictable production of the desired microbial output. The control systems can be monitored by a technician or an automated system.

Phase Data Sets

Phase data sets are sets of measurements of physical properties of the physical containment system and the working fluid. The phase data sets characterize the biological activity occurring in each phase space. Phase data sets are used to provide feedback to the process controls that enable alteration of conditions in the physical containment system to control the biology contained therein. The phase data sets are continuously monitored to ensure consistency of the final microbial output product.

Phase data sets include parameters of pressure, chemical, biological, flow rate, composition, temperature, and temporal data. The phase data includes organic feed rate, hydraulic feed rate, internal feed rate, temperature level, pH level, chemical oxygen demand (COD) level, conductivity level, hydraulic dwell time, microbial size type, microbial configuration, numerical sequencing, and volume, type or configuration of output product. Organic feed rate, hydraulic feed rate, internal recycle rate, temperature level, pH level, COD level, conductivity level, and hydraulic dwell time are measured. The working fluid in the physical containment system is maintained at constant pressure.

Controlling the Phase Profile

Careful regulation of hydraulic loading rates, feed rates, dwell times and hydraulic shear through recycle rates in the physical containment system in each phase space regulates growth of colonization by the microbes in the working fluid and promotes and controls growth of biofilm. The control of hydraulic loading rates and dwell times minimizes competition between preferred species of microbes and maximizes reaction efficiency in each phase to increase biofilm development.

Figure 2:
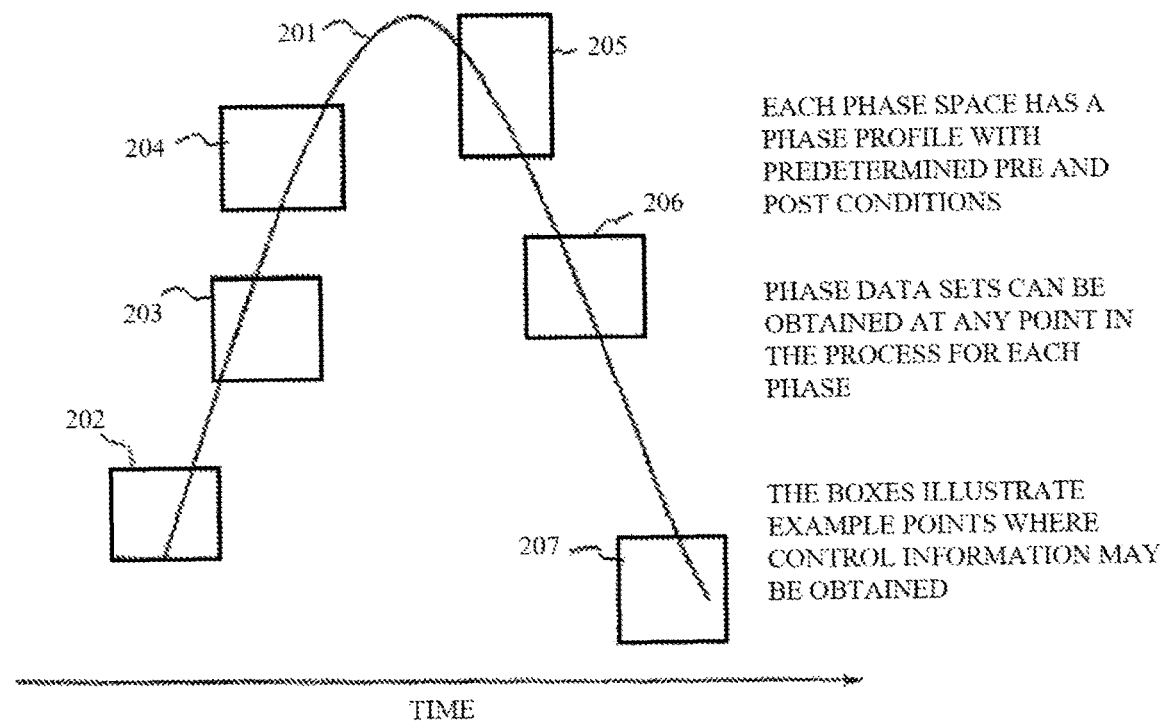
FIG. 2 is an illustration of a phase space, execution of processing and sample points where control information may be obtained.

Referring to FIG. 2, a graph of a phase space executing phase 201 and illustrating execution of process management control points is shown. At the sample points, phase data sets 202, 203, 204, 205, 206, and 207 of information are obtained. In one embodiment, phase data sets 202, 203, 204, 205, 206, and 207 are measured by removing samples of the working fluid during the phases. An aliquot of the working fluid is taken to represent an exact fraction of each phase space. Extracting the aliquot of the working fluid to create the phase data set can be done manually. In other embodiments, phase data sets 202, 203, 204, 205, 206, and 207 are measured by automated sampling using data acquisition sensors connected to analytic devices that are connected to diverter collection terminals and a process controller that provide output data results.

In one embodiment, phase data sets 202, 203, 204, 205, 206, and 207 are presented to an operator who manually manipulates the various system controls of the reactor system. In this embodiment, manual operators use a set of instructions to adjust the system by opening or closing valves, flow rates, temperature or other parameters in response to phase data sets 202, 203, 204, 205, 206, and 207. Control inputs to alter pre- and post-conditions are calculated using tables or predictive equations which generate control input to the physical containment system to achieve predicted or empirical results. In another embodiment, a centralized computer processor is connected by a network to the sensors and is used to analyze and compare phase data sets 202, 203, 204, 205, 206, and 207 against the phase profiles and apply stored lookup tables or predictive equations to generate control feedback to the physical containment system. In yet another embodiment, a combination of manual and automated controls is used.

Operation of the Physical Containment System

Figure 3:
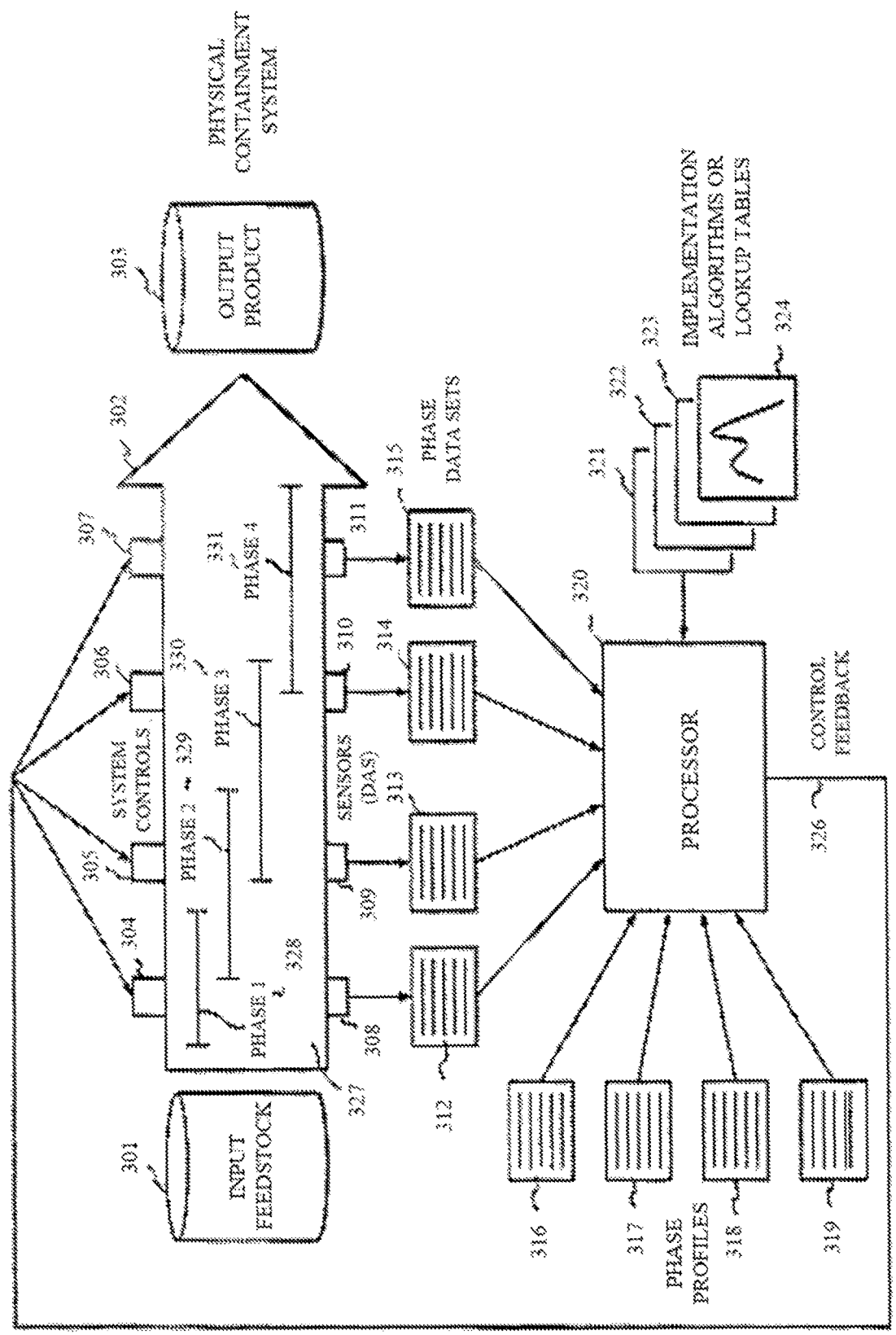
FIG. 3 is a schematic diagram of the preferred embodiment.

Referring to FIG. 3, physical containment system 302 is provided which houses and directs a constant flow of working fluid 327 from input feedstock 301 to microbial output product 303. Physical containment system 302 includes system controls 304, 305, 306, and 307, which are, in a preferred embodiment, pumps, valves, heaters, venting systems, timers, and waste solid outlets to effect biological changes to working fluid 327.

Physical containment system 302 includes data acquisition sensors 308, 309, 310, and 311 for monitoring parameters in physical containment system 302. Data acquisition sensors (DAS) 308, 309, 310, and 311 provide data used for monitoring first phase 328, second phase 329, third phase 330, and fourth phase 331 in a series of phase data sets 312, 313, 314, and 315. Phase data sets 312, 313, 314, and 315 are typically stored in the memory of a computer system which can be a general purpose digital computer or a set of dedicated controllers or other automated digital controls familiar to one skilled in the art. Data acquisition sensors 308, 309, 310, and 311 can provide output data used to manually adjust physical containment system 302 in the form of print outs, displays on computer screens of digital devices.

In other embodiments, data acquisition sensors 308, 309, 310, and 311 may be physically adjacent to the system controls so that feedback from data acquisition sensors 308, 309, 310, and 311 can be localized and implemented by system controls 304, 305, 306, and 307.

Figure 4:
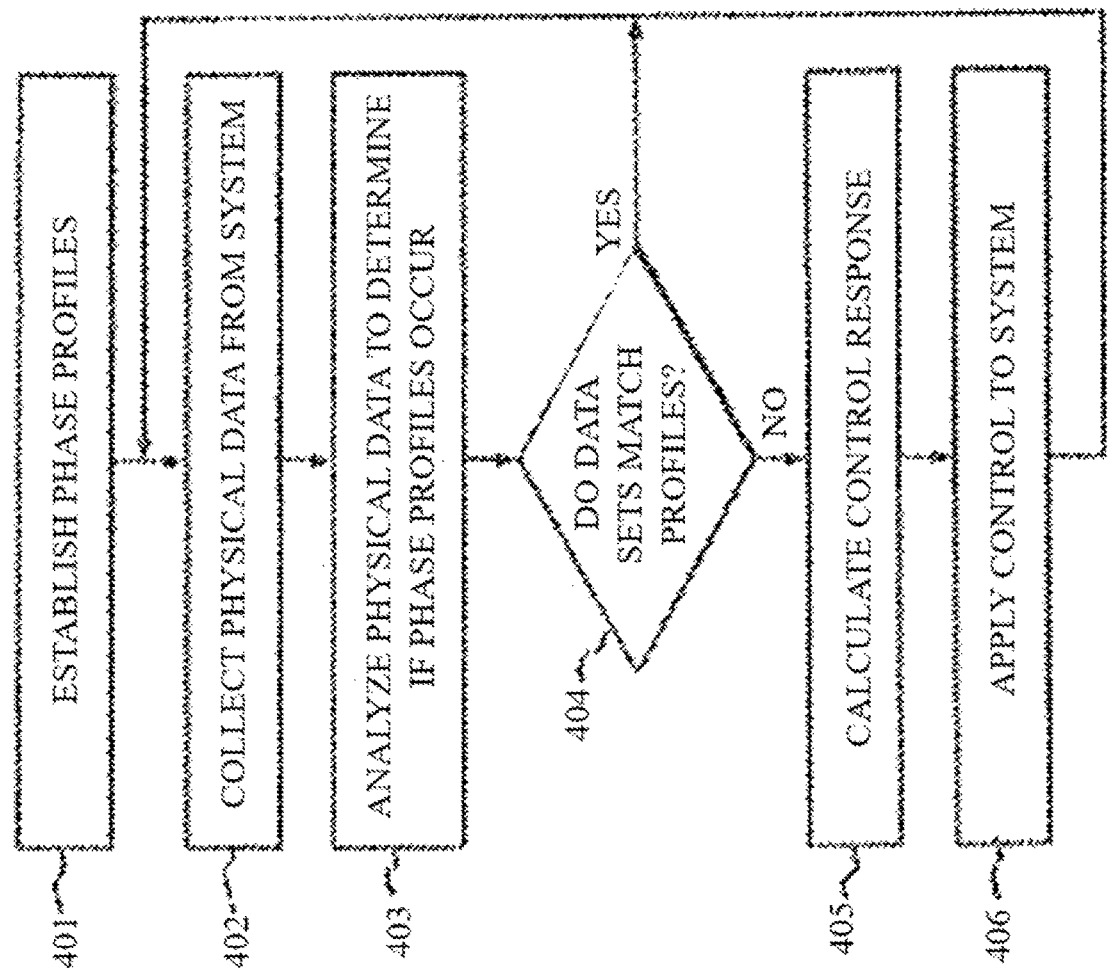
FIG. 4 is a flowchart of a system process using phase spaces, phase profiles, and phase data sets for creation of microbial output.

Referring to FIGS. 3 and 4, phase profiles 316, 317, 318, and 319 for each phase of physical containment system 302 are established from desired characteristics or modes of each phase and the desired microbial output product 303 in step 401. Each of phase data sets 312, 313, 314, and 315 are collected from physical containment system 302 in step 402 by data acquisition sensors 308, 309, 310, and 311 and respectively compared to phase profiles 316, 317, 318, and 319 by processor 320 in step 403. In step 404, a potential match of the phase data set to the respective phase profile is determined. If phase data sets 312, 313, 314, and 315 respectively match phase profiles 316, 317, 318, and 319, then system controls 304, 305, 306, and 307 are not adjusted and steps 402 and 403 are repeated throughout the process.

If any of phase data sets 312, 313, 314, and 315 do not respectively match any of phase profiles 316, 317, 318, and 319, then processor 320 consults predictive equations or lookup tables 321, 322, 323, or 324 to calculate control feedback 326 in step 405. Once calculated, control feedback 326 is sent to one of system controls 304, 305, 306, or 307 which alters the physical parameters of physical containment system 302 in order to adjust the biological processes taking place in working fluid 327 to match phase profiles 316, 317, 318, and 319 in step 406. Steps 402, 403, 404, and 405 are then repeated throughout the process.

Waste management as part of system controls 304, 305, 306, and 307 optimizes microbial development in physical containment system 302. Waste removal facilitates the growth of desired microbial communities free from the buildup of waste materials that might stunt, prevent, or otherwise interfere with the growth of these communities and the production of desired by-products. Waste products may include liquids, gases, or solids.

In one embodiment, waste solids in the form of settled solids/sludge is monitored and maintained to be in a range of approximately 10% to 15% settled solids by volume with a 30 minute static test. Settled waste solids are manually removed from every vessel of physical containment system 302 as necessary to maintain the proper level of settled solids.

In another embodiment, when any of data acquisition sensors 308, 309, 310, or 311 detects that the amount of settled solids exceeds a predetermined range of approximately 10% to 15% settled solids, an alert is generated on a display for further attention. The settled solids are automatically removed from every vessel of physical containment system 302 by system controls 304, 305, 306, and 307 as necessary to maintain the proper level of settled solids.

In another embodiment, the settled solids are determined through the amount of total dissolved solids (TDS). TDS is the amount of solid material in a colloidal suspension. The amount of TDS is determined through tests known in the art. These tests can be conducted automatically by any of data acquisition sensors 308, 309, 310, and 311 or manually by samples to measure the amount of TDS. The amount of TDS is then used to determine the amount of settled solids through methods known in the art. The amount of settled solids is maintained to be in a range of approximately 10% to 15% settled solids by volume. Settled solids are removed from every vessel of physical containment system 302 as necessary to maintain the predetermined range of settled solids.

Gaseous waste is managed as part of system controls 304, 305, 306, and 307. Gaseous waste in the form of hydrogen sulfide is vented through terminals connected to each vessel of physical containment system 302 and further connects to a gas collection system. The gas collection system comprises a gas scrubber that neutralizes waste gases before venting and elimination from physical containment system 302.

Physical containment system 302 is initially supplied with input feedstock 301 comprising an organic feedstock of dairy cow manure, make-up water, and process feed water. Make-up water and process feed water can come from various sources. In this embodiment, the process feed water source is permeate water recycled from a nano filtration system and the make-up water is municipal water. Input feedstock 301 becomes working fluid 327 upon entering into physical containment system 302.

Working fluid 327 is continuously recycled or mixed in a holding tank to prevent premature aging and septic development. Working fluid 327 is managed to maintain a concentration of liquid manure in the holding tank by COD measurement. The COD in this embodiment is in a range of approximately 10,000 mg/L to 40,000 mg/L.

In this embodiment, the temperature of the holding tank may vary from 20° to 45° Centigrade (C), but the variance across the phases should not be greater than 4° C. to preserve the stability within and across physical containment system 302.

The temperature may be monitored by a variety of methods, from manual insertion and reading from simple probes to ongoing monitoring through installed sensors. Temperature may be adjusted, at any stage of physical containment system 302 by either manual input or system controls 304, 305, 306, and 307. The temperature is controlled by a non-contacting hot water heating tube preferably attached to each vessel. Piped header systems may be connected to modulating valves that may be operated manually or with motorized controllers that are connected to process control systems programmed to maintain the individual vessels. These heating pipes may be attached to a low temperature condensing boiler system. Other process heating methods, such as heat tracing of individual vessels may be employed with equal success.

Complete Mix Reactor (CMR) and Clarifier (CLR)

The first phase space of physical containment system 302 comprises a complete mix reactor (CMR) connected to the holding tank and coupled with a clarifier. First phase 328 begins when working fluid 327, i.e., the organic feedstock, and the water, are fed into the CMR.

Nutrient supplements may be added to working fluid 327. Nutrient supplements can be added manually or automatically. In one embodiment, dry active yeast is added to working fluid 327. In this embodiment, the dry active yeast is pre-mixed with water and added to the CMR at a controlled rate of 1 lb. of yeast per 5000 gallons of hydraulic feed per day.

In another embodiment, working fluid 327 is automatically pumped into the CMR and the nutrient supplements are added to the holding tank and controlled by valves, pumps and sensors to deliver the amount of supplement programmed as a pre-condition for the mixing of input feedstock 301 and nutrient supplements in the CMR. In this embodiment, the nutrient supplements are added in a 1:1 to 1:10 ratio, preferably a 1:5 ratio of nutrient supplement to 1 lb. of the organic feedstock.

In another embodiment, an aliquot of a second working fluid extracted from a previously existing system may be added to working fluid 327 as an optional additional nutrient supplement. The second working fluid from the previously existing system is extracted as the second working fluid moves to the stabilization phase and is added to working fluid 327 in an amount between one and five gallons of the aliquot. Alternatively, the second working fluid from a previously existing physical containment system may be added to an inert, water soluble carrier, preferably composed of calcium carbonate, and added to working fluid 327 at an amount equivalent to the liquid addition described above.

In a preferred embodiment, the organic feedstock is fed into the CMR at the organic feed rate of 0.001-0.1 lbs. of organic feedstock per cubic foot of total system working capacity per day. In this embodiment, the ratio of the organic feedstock to water is in a range of 10:1 to 2:1, 10 units of total working capacity to 1 unit of feed water.

In one embodiment, the combination of organic feed rate and hydraulic loading rate can be mathematically expressed as follows:

Combined Loading Rate=(0.001 to 0.1 lbs. Organic Feedstock/ft$^3$

Reactor fixed media Volume/Day)+(0.2 to 2 lb. Dry Active Yeast/5,000 gals. Hydraulic Fresh Water Input) @ 28 to 40 degrees C., yields stable processed material product in 5 to 14 days of system HDT (Hydraulic Dwell Time).

In a particular embodiment, the combination of organic feed rate and hydraulic loading rate can be mathematically expressed as follows:

Combined Loading Rate=(0.01 lbs. Organic Feedstock/ft$^3$ Reactor fixed media Volume/Day)+(1 lb. Dry Active Yeast/5,000 gals. Hydraulic Fresh Water Input) @ 34 C., yields stable processed material product in 7 days of system HDT (Hydraulic Dwell Time).

For example, if the total working reactor has a capacity of 224,000 gallons, then, at a 7:1 ratio, feed water is fed into the CMR at a rate of 32,000 gallons per day or 22.222 gallons per minute having a seven day system hydraulic dwell time.

In a preferred embodiment, working fluid 327 in the CMR is recycled or mixed at a rate ratio in a range of approximately 20:1 to 40:1 gallons per minute of the recycle rate to one gallon per minute of the hydraulic feed rate to promote hydrolysis and to prevent buildup of settled solids. The mixing is periodically halted in order to allow for separation and return of organic solids within physical containment system 302 and the wasting of unusable cellulose and other mix related byproducts from the system. In another embodiment, working fluid 327 is mixed at varying speeds.

Various mechanical methods of mixing can be employed in various embodiments. For example, vented pressure release through internal piping, jet streams, pumps and piping, and rotating blades can be used with equal success. Other methods of mixing will be apparent to one of skill in the art.

After a predetermined dwell time, working fluid 327 is transferred to the clarifier. In the clarifier, suspended solids separate from solution, producing a supernatant comprised of dissolved and colloidal organics. Solids settle to the bottom of the clarifier and are returned to the CMR with a circulation pump or induction system. In this embodiment, settled solids are returned from the bottom of the clarifier to the CMR at a ratio range of 1:1 to 1:10, one gallon of settled solids for every one gallon of hydraulic loading to one gallon of settled solids for every ten gallons of hydraulic loading. In another embodiment, the ratio is 1:4.5 where one gallon of settled solids for every 4.5 gallons of hydraulic loading is returned. Settled solids are managed in the CMR and the clarifier to maintain a range of 10% to 15% settled solids as previously described.

Aliquots of working fluid 327 may be taken from the CMR to analyze the chemical balance. The aliquot of working fluid 327 may be manually transferred to another processing system or another physical containment system for processing against an alternative phase profile for an alternative output.

The CMR and the clarifier are monitored through data acquisition sensor 308 for: pH, which is preferably in a range of approximately 6.2 to 7.9; COD, which is preferably in a range of approximately 400 mg/L to 2000 mg/L; and conductivity, which is preferably in a range of approximately 500 μS to 2000 μS. In this embodiment, data acquisition sensor 308 feeds data to a supervisory control and data acquisition (SCADA) systems process controller that regulates temperature and loading rates based on sensory inputs and preset ranges. The SCADA systems process controller of this embodiment is a personal computer having processor 320 and connected by a network to data acquisition sensors 308, 309, 310, and 311 in physical containment system 302.

After a predetermined dwell time in the CMR and the clarifier of the first phase space, working fluid 327 is transferred from the clarifier to a first set of a series of packed bed reactors (PBRs) of the second phase space at a hydraulic feed rate range of approximately 0.5 to 2.0 gallons per minute. Second phase 329, third phase, 330, and fourth phase 331 primarily take place in the PBRs.

Packed Bed Reactors

In this embodiment, each of the packed bed reactors has an open cell design to allow free movement of working fluid 327. A fixed media is secured to the inside of each packed bed reactor. The fixed media comprises materials that increase the contact surface area for the communities of microbes with working fluid 327. The fixed media also provides a stable platform for anchoring biofilm. The fixed media can be of several types, including durable plastic, polyvinyl chloride (PVC), metal, metal alloy, glass, glass compounds, fiberglass, or any suitably robust inert material. The design and configuration of the fixed media can assume various geometric patterns that allow working fluid 327 to freely move through each packed bed reactor and prevents fouling. Free flow supports controlled hydraulic shearing which in time promotes even distribution of working fluid 327. In this embodiment, the fixed media is dispersed throughout a cross sectional area of each packed bed reactor.

In this embodiment, working fluid 327 in each reactor is continuously recycled at a rate ratio in a range of approximately 25:1 to 35:1, 25 to 35 gallons per minute of the recycle rate to one gallon per minute of the hydraulic feed rate, preferably at a rate ratio of 30:1. Working fluid 327 is transferred in and out of each packed bed reactor at the hydraulic feed rate of approximately one gallon per minute. Working fluid 327 is recycled by a pump to prevent solids settling and to provide sufficient velocity and hydraulic shear to prevent excessive buildup and sloughing of biofilm.

Settled solids are managed in each of the packed bed reactors of second phase 329, third phase 330, and fourth phase 331 to maintain a range of 10% to 15% settled solids as previously described.

EXAMPLES

The compositions, systems, apparatuses and methods set forth above will be further illustrated in the following, non-limiting Examples. The examples are illustrative of various embodiments only and do not limit the claimed invention regarding the materials, conditions, weight ratios, process parameters and the like recited herein.

Example 1: Four Phase Bioreactor

First Phase Numerical Results

Samples of working fluid 327 in first phase 328 are taken from physical containment system 302 and the microbes contained in the sample of working fluid 327 in first phase 328 are analyzed using pyrosequencing. From the pyrosequencing, microbes of first phase 328 were identified from sequences of PCR-amplified 16*s* rRNA gene fragments, called ribotypes, which confirms the efficacy of physical containment system 302 in first phase 328. Samples of the results of the analysis of first phase 328 are listed in Table 1 below.

TABLE 1

Abundance of Numerically Dominant Ribotypes in the First Phase

| Cluster[1] | Genus[2] | Metabolism | First phase |
|---|---|---|---|
| 12 | *Syntrophus* | methanogen | 54 |
| 55 | *Desulfovibrio* | sulfur-reducing | 25 |
| 195 | *Symbiobacteria* | dechlorination | 24 |
| 16 | *Georgfuchsia* | aromatic degrading | 30 |
| 21 | *Thauera* | denitrifier | 0 |
| 1 | *Flavobacterium* | denitrifier | 0 |
| 9 | *Nitrosomonas* | nitrification | 1 |
| 11 | *Sedimini-bacterium* | heterotroph | 0 |
| 2 | *Nitrosomonas* | nitrification | 0 |
| 22 | *Methlylomonas* | methanotroph | 0 |
| 13 | *Bellilinea* | anaerobe | 0 |
| 5 | *Sulfuritalea* | sulfur-oxidation | 0 |
| 59 | *Owenweeksia* | anamox | 0 |
| 4 | *Sphingomonas* | high $CO_2$ | 0 |
| 6 | n.a.[3] | methanogen | 1 |
| 5 | n.a.[3] | iron-oxidation | 1 |

[1]Group of sequences clustered together based on similarity.
[2]Classification of ribotype at the genus level.
[3]Reliable classification not possible.

The processes of first phase 328 generally occur under strict anaerobic conditions when more thermodynamically favorable electron acceptors, like oxygen and nitrate, have been exhausted. Ribotypes related to *Symbiobacteria*, *Syntrophus*, and *Georgfuchsia* are present in sufficient quantity to indicate dominance in first phase 328. Isolates and communities associated with these genera are capable of converting complex organics, such as aromatics and chlorinated hydrocarbons into more labile compounds. This degradation is associated with methane production and sulfate reduction in first phase 328.

In this embodiment, the temperature of the first phase space may vary from 29° C. to 39° C., but the variance across phases should not be greater than 4° C. to preserve the stability within and across physical containment system 302.

The temperature may be monitored by a variety of methods, from manual insertion and reading from simple probes to ongoing monitoring through data acquisition sensor 308. Temperature of the first phase space may also be adjusted by either manual input or by system control 304. The temperature is controlled by a non-contacting hot water heating tube as previously described. Mechanized valves and controllers connected to system control 304 programmed to maintain predetermined temperature levels may be employed with the CMR and clarifier as previously described.

In this embodiment, the hydraulic dwell time for working fluid 327 in the CMR and the clarifier is in a range of approximately 1 to 5 days.

First Phase Lookup Table

In this embodiment, phase profile 316 of first phase 328 includes ranges of pH, COD, conductivity and temperature. Data acquisition sensor 308 for monitoring each of these parameters is attached inside or adjacent to each vessel. Data is acquired from data acquisition sensor 308 on a continuous basis to form phase data set 312 of first phase 328.

Phase data set 312 is periodically compared to phase profile 316. In one embodiment, the comparison is made manually. In another embodiment, the comparison is made using processor 320. If the comparison shows that phase data set 312 does not match phase profile 316, then lookup table 321 is consulted and applied as control feedback 326 according to Table 2 below.

TABLE 2

First Phase Lookup Table

| Phase Data Comparison Result | Control Input |
|---|---|
| pH level is low | Increase hydraulic load rate to internal recycle rate ratio; increase organic load rate; decrease dwell time |
| pH level is high | Decrease hydraulic load rate to internal recycle rate ratio; increase dwell time; decrease organic load rate |
| COD is low | Increase hydraulic load rate to internal recycle rate ratio; increase organic load rate; decrease dwell time |
| COD is high | Decrease hydraulic load rate to internal recycle rate ratio; increase dwell time; decrease organic load rate |
| Conductivity is low | Increase hydraulic load rate to internal recycle rate ratio; increase organic load rate; decrease dwell time |
| Conductivity is high | Decrease hydraulic load rate to internal recycle rate ratio; increase dwell time; decrease organic load rate |
| Temperature is low | Increase circulation of hot water circulation within heating tube |
| Temperature is high | Decrease circulation of hot water circulation within heating tube |

Second Phase Space

After the predetermined hydraulic dwell time in the CMR and the clarifier of the first phase space, working fluid 327 is transferred from the first phase space to the second phase space.

Second phase 329 primarily comprises acidogenesis and acetogenesis. Second phase 329 primarily takes place in the second phase space in the packed bed reactors.

In this embodiment, the recycle rate ratio is in a range of approximately 25:1 to 35:1. The second phase space is monitored through data acquisition sensor 309 for: pH, which is preferably in a range of approximately 6.0 to 8.0; COD, which is preferably in a range of approximately 100 mg/L to 400 mg/L; and conductivity, which is preferably in a range of approximately 1000 µS to 1600 µS.

Second Phase Numerical Results

Samples of working fluid 327 in second phase 329 are from taken physical containment system 302 and microbes contained in the sample of working fluid 327 in second phase 329 are analyzed using pyrosequencing. From the pyrosequencing, the microbes of second phase 329 are identified from sequences of PCR-amplified 16s rRNA gene fragments, called ribotypes, which confirms the efficacy of physical containment system 302 in second phase 329. Samples of the results of the analysis of second phase 329 are listed in Table 3.

TABLE 3

Abundance of Numerically Dominant Ribotypes in the Second Phase

| Cluster[1] | Genus[2] | Metabolism | Second Phase |
|---|---|---|---|
| 12 | *Syntrophus* | methanogen | 1 |
| 55 | *Desulfovibrio* | sulfur-reducing | 0 |
| 195 | *Symbiobacteria* | dechlorination | 2 |
| 16 | *Georgfuchsia* | aromatic degrading | 1 |
| 21 | *Thauera* | denitrifier | 24 |
| 1 | *Flavobacterium* | denitrifier | 16 |
| 9 | *Nitrosomonas* | nitrification | 43 |
| 11 | *Sedimini-bacterium* | heterotroph | 0 |
| 2 | *Nitrosomonas* | nitrification | 0 |
| 22 | *Methlylomonas* | methanotroph | 0 |
| 13 | *Bellilinea* | anaerobe | 0 |
| 5 | *Sulfuritalea* | sulfur-oxidation | 0 |
| 59 | *Owenweeksia* | anamox | 1 |
| 4 | *Sphingomonas* | high $CO_2$ | 1 |

TABLE 3-continued

Abundance of Numerically Dominant Ribotypes in the Second Phase

| Cluster[1] | Genus[2] | Metabolism | Second Phase |
|---|---|---|---|
| 6 | n.a.[3] | methanogen | 0 |
| 5 | n.a.[3] | iron-oxidation | 0 |

[1]Group of sequences clustered together based on similarity.
[2]Classification of ribotype at the genus level.
[3]Reliable classification not possible.

Second phase 329 represents a transition zone between first phase 328 and third phase 330. Numerically, nitrifiers dominate second phase 329, but the relative abundance of this group of bacteria peaks in third phase 330. Ribotypes that show similarity to the genus *Thauera* and the species *Flavobacterium filum* are dominant in second phase 329. These groups of bacteria are capable of denitrification.

Gaseous waste is managed as part of system control 305. Gaseous waste in the form of hydrogen sulfide is vented through terminals connected to each vessel of the second phase space and further connects to a gas collection system. The gas collection system comprises a gas scrubber that neutralizes waste gases before venting and elimination from the second phase space.

The temperature of the second phase space may vary from 29° C. to 39° C., but the variance across phases should not be greater than 4° C. to preserve the stability within and across physical containment system 302. The temperature may be monitored by a variety of methods, from manual insertion and reading from simple probes to ongoing monitoring through data acquisition sensor 309. Temperature in the second phase space may also be adjusted, by either manual input or by system control 305. The temperature is controlled by a non-contacting hot water heating tube as previously described. Piped header systems may be connected to mechanical valves and controllers as previously described.

In this embodiment, the hydraulic dwell time for working fluid 327 within the second phase space is in a range of approximately 1 to 4 days. The recycle rate ratio is in a range of approximately 25:1 to 35:1.

Second Phase Lookup Table

In this embodiment, data acquisition sensor 309 located in or adjacent to the PBRs of the second phase space collects data as phase data set 313 of second phase 329 including pH level, COD, conductivity, and temperature. Phase data set 313 is compared to phase profile 317 second phase 329. If phase data set 313 matches phase profile 317, no system control change is made. If phase data set 313 does not match phase profile 317, lookup table 322 is consulted for control feedback 326 to be made to system control 305 of physical containment system 302 in order to adjust the parameters toward phase profile 317. In this embodiment, system control 305 is adjusted manually in some instances and automatically in others.

Data acquisition sensor 309 sends data to a SCADA systems process controller having processor 320 that regulates temperature, loading rates, recycle rates, and hydraulic feed rates based on sensory inputs and preset ranges. Control feedback 326 is applied for second phase 329 according to Table 4.

TABLE 4

Second Phase Lookup

| Phase Data Comparison Result | Control Input |
|---|---|
| pH level is low | Increase hydraulic feed rate to internal recycle rate ratio; decrease dwell time |
| pH level is high | Decrease hydraulic feed rate to internal recycle rate ratio; increase dwell time |
| COD is low | Increase hydraulic feed rate to internal recycle rate ratio; decrease dwell time |
| COD is high | Decrease hydraulic feed rate to internal recycle rate ratio; increase dwell time |
| Conductivity is low | Increase hydraulic feed rate to internal recycle rate ratio; decrease dwell time |
| Conductivity is high | Decrease hydraulic feed rate to internal recycle rate ratio; increase dwell time |
| Temperature is low | Increase circulation of hot water circulation within heating tube |
| Temperature is high | Decrease circulation of hot water circulation within heating tube |

Third Phase Space

After the predetermined hydraulic dwell time in the second phase space, working fluid 327 is transferred from the second phase space to a third phase space. Working fluid 327 is transferred from the second phase space to the third phase space at the hydraulic feed rate of one gallon per minute, which may be adjusted to be proportional to the total volume of the second phase space to maintain the predetermined balance of hydraulic dwell times and organic loading of physical containment system 302.

Third Phase 330 Comprises Primarily Methanogenesis.

The third phase space monitored through data acquisition sensor 310 for: pH, which is preferably in a range of approximately 7.0 to 8.0; COD, which is preferably in a range of approximately 100 mg/L to 400 mg/L; and conductivity, which is preferably in a range of approximately 700 µS to 1500 µS.

Third Phase Numerical Results

Samples of working fluid 327 in third phase 330 are taken from physical containment system 302 and microbes contained in the sample of working fluid 327 of third phase 330 are analyzed using pyrosequencing. From the pyrosequencing, the microbes of third phase 330 are identified from sequences of PCR-amplified 16s rRNA gene fragments, called ribotypes, which confirmed the efficacy of physical containment system 302 in third phase 330. Samples of the results of the analysis of the sample of working fluid 327 in third phase 330 are listed in Table 5 below.

TABLE 5

Abundance of Numerically Dominant Ribotypes in the Third Phase

| Cluster[1] | Genus[2] | Metabolism | Third phase |
|---|---|---|---|
| 12 | *Syntrophus* | methanogen | 0 |
| 55 | *Desulfovibrio* | sulfur-reducing | 0 |
| 195 | *Symbiobacteria* | dechlorination | 0 |
| 16 | *Georgfuchsia* | aromatic degrading | 1 |
| 21 | *Thauera* | denitrifier | 0 |
| 1 | *Flavobacterium* | denitrifier | 11 |
| 9 | *Nitrosomonas* | nitrification | 452 |
| 11 | *Sedimini-bacterium* | heterotroph | 83 |
| 2 | *Nitrosomonas* | nitrification | 54 |
| 22 | *Methylomonas* | methanotroph | 40 |
| 13 | *Bellilinea* | anaerobe | 0 |
| 5 | *Sulfuritalea* | sulfur-oxidation | 0 |
| 59 | *Owenweeksia* | anamox | 0 |

TABLE 5-continued

Abundance of Numerically Dominant Ribotypes in the Third Phase

| Cluster[1] | Genus[2] | Metabolism | Third phase |
|---|---|---|---|
| 4 | Sphingomonas | high $CO_2$ | 39 |
| 6 | n.a.[3] | methanogen | 0 |
| 5 | n.a.[3] | iron-oxidation | 0 |

[1]Group of sequences clustered together based on similarity.
[2]Classification of ribotype at the genus level.
[3]Reliable classification not possible.

The processes in third phase 330 oxidize elements reduced by microbial processes in first phase 328. Methanotrophy and nitrification dominate third phase 330. Methanotrophs oxidize methane to carbon dioxide, thereby generating adenosine triphosphate (ATP). Nitrifiers oxidize ammonium to nitrite and nitrate through a form of chemolithotrophy. Both of these groups of microbes require oxygen. Nitrifiers grow slowly and require establishment of a mature community to oxidize ammonium completely to nitrate. Methanotrophs grow rapidly and scavenge available methane, thereby reducing the amount of methane produced.

Gaseous waste is managed as part of system control 306. Gaseous waste in the form of hydrogen sulfide is vented through terminals connected to each vessel of the third phase space and further connects to a gas collection system. The gas collection system comprises a gas scrubber that neutralizes waste gases before venting and elimination from the third phase space.

The temperature of the third phase space may vary from 29° C. to 39° C., but the variance across phases should not be greater than 4° C. to preserve the stability within and across physical containment system 302. The temperature may be monitored by a variety of methods, from manual insertion and reading from simple probes to ongoing monitoring through data acquisition sensor 310. Temperature may also be adjusted in the third phase space by either manual input or by system control 306. The temperature is controlled by a non-contacting hot water heating tube as previously described. Piped header systems may be connected to mechanical valves and controllers as previously described.

The hydraulic dwell time for working fluid 327 within the third phase space is in a range of approximately 1 to 4 days. The recycle rate ratio is in a range of approximately 25:1 to 35:1.

Third Phase Lookup Table

In this embodiment, data acquisition sensor 310 is located in or adjacent to the PBRs which make up physical containment system 302 for the third phase space. Data acquisition sensor 310 sends data to a SCADA systems process controller having processor 320 that regulates temperature, loading rates, recycle rates, and hydraulic feed rates based on sensory inputs and preset ranges. Phase data set 314 of third phase 330 is compared to phase profile 318 of third phase 330. If the comparison shows that phase data set 314 matches phase profile 318, no system control change is made. If phase data set 314 does not match phase profile 318, lookup table 323 is consulted in order to determine control feedback 326 for physical containment system 302. Control feedback 326 is made through system control 306, which includes mechanisms such as valves and motor controllers to alter the conditions of physical containment system 302. Control feedback 326 for third phase 330 is determined by Table 6 below.

TABLE 6

Third Phase Lookup Table

| Phase Data Comparison Result | Control Input |
|---|---|
| pH level is low | Increase hydraulic feed rate to internal recycle rate ratio; decrease dwell time |
| pH level is high | Decrease hydraulic feed rate to internal recycle rate ratio; increase dwell time |
| COD is low | Increase hydraulic feed rate to internal recycle rate ratio; decrease dwell time |
| COD is high | Decrease hydraulic feed rate to internal recycle rate ratio; increase dwell time |
| Conductivity is low | Increase hydraulic feed rate to internal recycle rate ratio; decrease dwell time |
| Conductivity is high | Decrease hydraulic feed rate to internal recycle rate ratio; increase dwell time |
| Temperature is low | Increase circulation of hot water circulation within heating tube |
| Temperature is high | Decrease circulation of hot water circulation within heating tube |

Fourth Phase Space

After the predetermined hydraulic dwell time in the third phase space, working fluid 327 is transferred from the third phase space to a fourth phase space. Working fluid 327 is transferred from the third phase space to the fourth phase space at the hydraulic feed rate of one gallon per minute, which may be adjusted to be proportional to total volume of the third phase space to maintain the predetermined balance of hydraulic dwell times and organic loading of physical containment system 302.

Fourth Phase 331 Comprises Primarily Reversion and Stabilization

The fourth phase space is monitored through data acquisition sensor 311 for: pH, which is in a range of approximately 7.6 to 8.3; COD, which is in a range of approximately 80 mg/L to 150 mg/L; and conductivity, which is in a range of approximately 900 µS to 1200 µS.

Fourth Phase Numerical Results

Samples of working fluid 327 in fourth phase 331 are taken from physical containment system 302 and microbes contained the sample of working fluid 327 in fourth phase 331 are analyzed using pyrosequencing. From the pyrosequencing, the microbes of fourth phase 331 are identified from sequences of PCR-amplified 16s rRNA gene fragments, called ribotypes, which confirmed the efficacy of physical containment system 302 in fourth phase 331. In addition, samples of the biofilm in fourth phase 331 are collected from the fourth phase space. the microbes in the biofilm in fourth phase 331 are analyzed using pyrosequencing. A sample of the results of the analysis of fourth phase 331 is listed in Table 7 below.

TABLE 7

Abundance of Numerically Dominant Ribotypes in the Fourth Phase

| Cluster[1] | Genus[2] | Metabolism | Fourth phase | Biofilm |
|---|---|---|---|---|
| 12 | Syntrophus | methanogen | 2 | 18 |
| 55 | Desulfovibrio | sulfur-reducing | 0 | 3 |
| 195 | Symbiobacteria | dechlorination | 0 | 2 |
| 16 | Georgfuchsia | aromatic degrading | 1 | 99 |
| 21 | Thauera | denitrifier | 46 | 34 |
| 1 | Flavobacterium | denitrifier | 0 | 0 |
| 9 | Nitrosomonas | nitrification | 152 | 1 |
| 11 | Sedimini-bacterium | heterotroph | 1 | 0 |
| 2 | Nitrosomonas | nitrification | 32 | 0 |

TABLE 7-continued

Abundance of Numerically Dominant Ribotypes in the Fourth Phase

| Cluster[1] | Genus[2] | Metabolism | Fourth phase | Biofilm |
|---|---|---|---|---|
| 22 | *Methlylomonas* | methanotroph | 0 | 0 |
| 13 | *Bellilinea* | anaerobe | 191 | 10 |
| 5 | *Sulfuritalea* | sulfur-oxidation | 4 | 66 |
| 59 | *Owenweeksia* | anamox | 1 | 163 |
| 4 | *Sphingomonas* | high $CO_2$ | 1 | 0 |
| 6 | n.a.[3] | methanogen | 3 | 164 |
| 5 | n.a.[3] | iron-oxidation | 3 | 125 |

[1]Group of sequences clustered together based on similarity.
[2]Classification of ribotype at the genus level.
[3]Reliable classification not possible.

The cycling of elements between surface-attached, or biofilm-associated, microbes and microbes suspended in working fluid 327 dominates the processes fourth phase 331, which completes the stabilization of microbial output product 303. Ribotypes generated from the collected samples of working fluid 327 in fourth phase 331 indicate similarity to species linked to nitrification, denitrification, and fermentation. All of these groups show relatively high numbers of ribotypes that show similarity to groups associated with anaerobic processes, including anaerobic ammonium oxidation (anamox), and methanogenesis.

Gaseous waste is managed as part of system control 307. Gaseous waste in the form of hydrogen sulfide is vented through terminals connected to each vessel of the fourth phase space and further connects to a gas collection system. The gas collection system comprises a gas scrubber that neutralizes waste gases before venting and elimination from the fourth phase space.

In this embodiment, the temperature of the fourth phase space may vary from 29° C. to 39° C., but the variance across phases should not be greater than 4° C. to preserve the stability within and across physical containment system 302.

The temperature may be monitored by a variety of methods, from manual insertion and reading from simple probes to ongoing monitoring through data acquisition sensor 311. Temperature may also be adjusted by either manual input or by system control 307. The temperature is controlled by a non-contacting hot water heating tube as previously described. Piped header systems may be connected to mechanized valves and controllers as previously described.

The hydraulic dwell time of working fluid 327 within the fourth phase space is in a range of approximately 1 to 4 days. After such time, microbial output product 303 produced from the phase spaces is sent through an outlet and accumulated in storage tanks or sent on for further optional processing, such as a pasteurizing or a concentration process. Working fluid 327 is transferred from the fourth phase space at the hydraulic feed rate of one gallon per minute, which may be adjusted to be proportional to total volume of the fourth space to maintain the predetermined balance of hydraulic dwell times and organic loading of physical containment system 302.

Fourth Phase Lookup Table

Phase data set 315 is acquired from data acquisition sensor 311 in or adjacent to the PBRs of fourth phase 331. Phase data set 315 of fourth phase 331 includes pH, COD, conductivity and temperature. Phase data set 315 is compared to phase profile 319 of fourth phase 331. If the comparison reveals no difference, then no control input is made to system control 307. However, if phase data set 315 does not match phase profile 319, lookup table 324 is consulted for the correct input for control feedback 326.

Data acquisition sensor 311 sends data to a SCADA systems process controller having processor 320 that regulates temperature, loading rates, recycle rates, and hydraulic feed rates based on sensory inputs and preset ranges. Control feedback 326 for fourth phase 331 is determined by Table 8 below.

TABLE 8

Fourth Phase Lookup Table

| Phase Data Comparison Result | Control Input |
|---|---|
| pH level is low | Increase hydraulic feed rate to internal recycle rate ratio; decrease dwell time |
| pH level is high | Decrease hydraulic feed rate to internal recycle rate ratio; increase dwell time |
| COD is low | Increase hydraulic feed rate to internal recycle rate ratio; decrease dwell time |
| COD is high | Decrease hydraulic feed rate to internal recycle rate ratio; increase dwell time |
| Conductivity is low | Increase hydraulic feed rate to internal recycle rate ratio; decrease dwell time |
| Conductivity is high | Decrease hydraulic feed rate to internal recycle rate ratio; increase dwell time |
| Temperature is low | Increase circulation of hot water circulation within heating tube |
| Temperature is high | Decrease circulation of hot water circulation within heating tube |

Example 2: Configuration of Discrete Vessels

Figure 5:
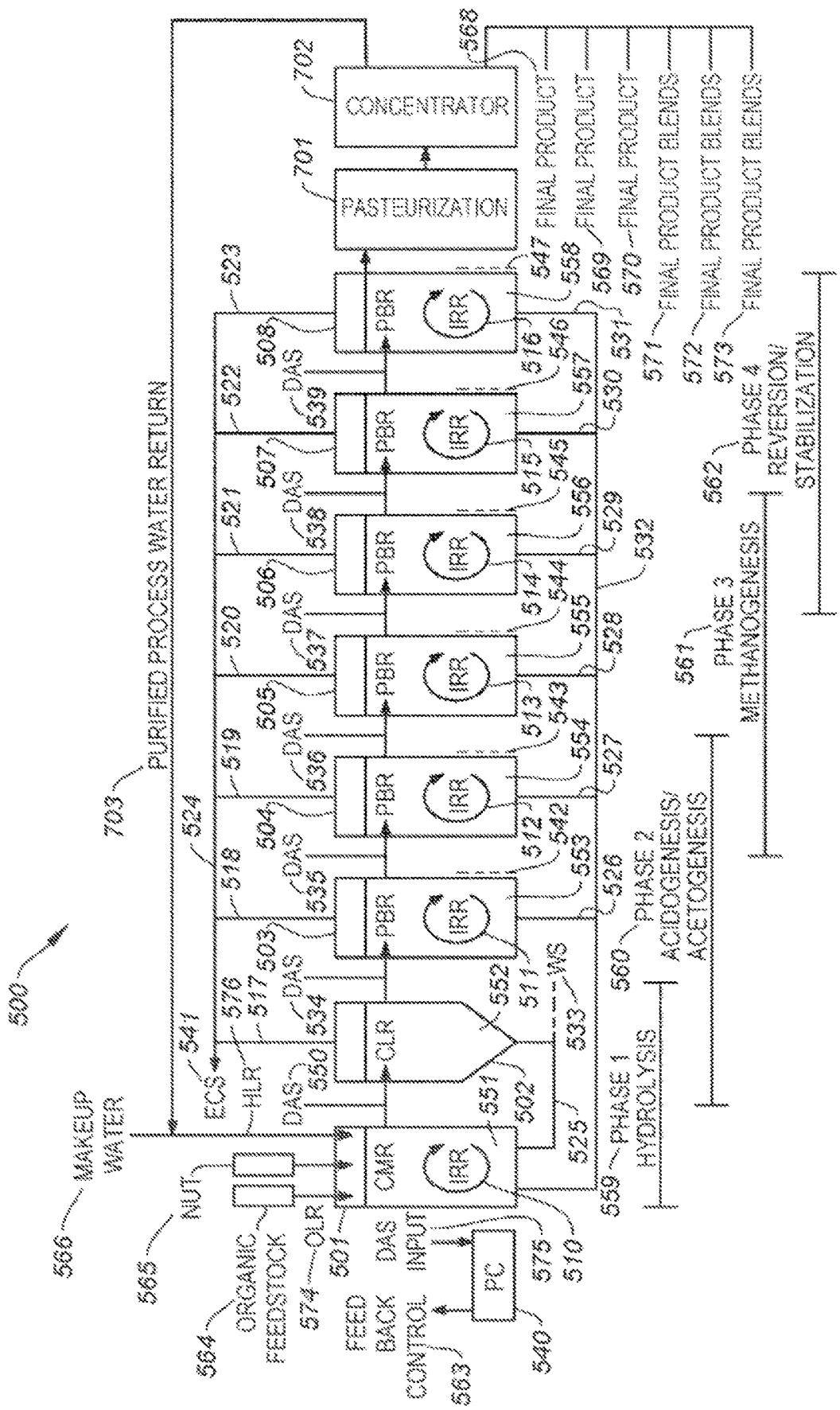
FIG. 5 is a diagram of the preferred embodiment.

Referring to FIG. 5 in one embodiment, physical containment system 500 comprises complete mix reactor 501, clarifier 502 connected to complete mix reactor 501, and a series of packed bed reactors 503, 504, 505, 506, 507, and 508 sequentially connected to clarifier 502, all of which cooperatively form the four phase spaces. Optionally, pasteurizer 701 may be connected to packed bed reactor 508 and concentrator 702 may be connected to pasteurizer 701. Concentrator 702 produces final microbial products 568, 569, and 570, and final microbial product blends 571, 572, and 573.

Packed bed reactors 503, 504, 505, 506, 507, and 508 comprise a set of separate vessels in sequential connection. Any number of vessels may be employed. If a greater number of vessels are used, greater control is gained over the process. It will be appreciated by those skilled in the art that other embodiments that exclude clarifier 502 are possible and are within the scope of this disclosure.

Organic feedstock 564 enters into complete mix reactor 501 at organic load rate 574. Nutrient supplements 565 enter into complete mix reactor 501. Makeup water 566 enters into complete mix reactor 501 at hydraulic load rate 576, forming working fluid 551.

Working fluid 551 is recycled within complete mix reactor 501 at internal recycle rate 510.

Packed bed reactors 503, 504, 505, 506, 507, and 508 recycle working fluids 553, 554, 555, 556, 557, and 558 within each packed bed reactor at internal recycle rates 511, 512, 513, 514, 515, and 516, respectively.

Gaseous waste vents 518, 519, 520, 521, 522, and 523 connect to packed bed reactors 503, 504, 505, 506, 507, and 508, respectively. Gaseous waste vents 518, 519, 520, 521, 522, and 523 connect to main gaseous waste vent 524. Main gaseous waste vent 524 connects to environmental control system 541 that scrubs noxious gases from the gaseous waste. Gaseous waste vent 517 connects to clarifier 502 and to main gaseous waste vent 524.

Waste solid outlets 526, 527, 528, 529, 530, and 531 connect to packed reactors 503, 504, 505, 506, 507, and 508, respectively. Waste solid outlets 526, 527, 528, 529, 530, and 531 connect to main waste solid outlet 532 to recycle waste solids from packed bed reactors 503, 504, 505, 506, 507, and 508 to complete mix reactor 501. Recycle connector 525 connects clarifier 502 to complete mix reactor 501 to recycle settled solids. Waste solid outlet 533 is connected to recycle connector 525 to drain waste solids.

In one embodiment, pumps and piping transfer and recycle working fluids 551, 552, 553, 554, 555, 556, 557, and 558. Other means known in the art may be employed.

In one embodiment, physical containment system 500 comprises unsealed vessels. In other embodiments, sealed vessels are employed. Further, the vessels of physical containment system 500 are not gated or separated in their entirety due to the process of balance, stability, and integrity across physical containment system 500. Each vessel or connected piping may employ diverter terminals attached to collection points that may transport working fluids 551, 552, 553, 554, 555, 556, 557, and 558 at any phase for analysis or parallel processing with an alternate processing system. In a preferred embodiment, gaseous venting and waste solids are discharged via valves and piping. Other means of gaseous venting and waste discharge known in the art may be employed.

Data acquisition sensor 550 connects to complete mix reactor 501 and clarifier 502, between complete mix reactor 501 and clarifier 502. Data acquisition sensor 550 further connects to process controller 540 at data acquisition sensor input 575. Data acquisition sensor 534 connects to clarifier 502 and packed bed reactor 503, between clarifier 502 and packed bed reactor 503. Data acquisition sensor 534 further connects to process controller 540 at data acquisition sensor input 575. Data acquisition sensor 535 connects to packed bed reactor 503 and packed bed reactor 504, between packed bed reactor 503 and packed bed reactor 504. Data acquisition sensor 535 further connects to process controller 540 at data acquisition sensor input 575. Data acquisition sensor 536 connects to packed bed reactor 504 and packed bed reactor 505, between packed bed reactor 504 and packed bed reactor 505. Data acquisition sensor 536 further connects to process controller 540 at data acquisition sensor input 575. Data acquisition sensor 537 connects to packed bed reactor 505 and packed bed reactor 506, between packed bed reactor 505 and packed bed reactor 506. Data acquisition sensor 537 further connects to process controller 540 at data acquisition sensor input 575. Data acquisition sensor 538 connects to packed bed reactor 506 and packed bed reactor 507, between packed bed reactor 506 and packed bed reactor 507. Data acquisition sensor 538 further connects to process controller 540 at data acquisition sensor input 575. Data acquisition sensor 539 connects to packed bed reactor 507 and packed bed reactor 508, between packed bed reactor 507 and packed bed reactor 508. Data acquisition sensor 539 further connects to process controller 540 at data acquisition sensor input 575. System controls such as pumps, valves, heaters 542, 543, 544, 545, 546, and 547, gas venting systems, timers, and waste solid outlets are connected to process controller 540 and, in conjunction with data acquisition sensors 550, 534, 535, 536, 537, 538, and 539, monitor the physical parameters of working fluids 551, 552, 553, 554, 555, 556, 557, and 558 and adjust the system controls with feedback control 563 in the same manner as previously described.

Still referring to FIG. 5, the phases overlap in the vessels of physical containment system 500. The physical locations of each phase along with their respective beginning, peak, and ending are approximate and are not limited to any particular physical vessel or section within a vessel. In this embodiment, first phase 559 begins in complete mix reactor 501, with the peak approximately occurring in complete mix reactor 501 and clarifier 502, and ending approximately between clarifier 502 and packed bed reactor 503.

Second phase 560 begins approximately in complete mix reactor 501 or clarifier 502, with the phase peak occurring approximately in clarifier 502, packed bed reactor 503, or packed bed reactor 504, and ending approximately in packed bed reactor 504 or packed bed reactor 505.

Third phase 561 begins approximately in packed bed reactor 503 or packed bed reactor 504, with the peak approximately in packed bed reactor 504, 505 and/or 506, and ending approximately in packed bed reactor 506 and/or 507.

Fourth phase 562 begins approximately in packed bed reactor 505 or 506, with the phase peak occurring approximately in packed bed reactor 506, 507, and/or 508, and ending in packed bed reactor 508.

Example 3: Embodiment Comprising a Continuous Tube

Figure 6:
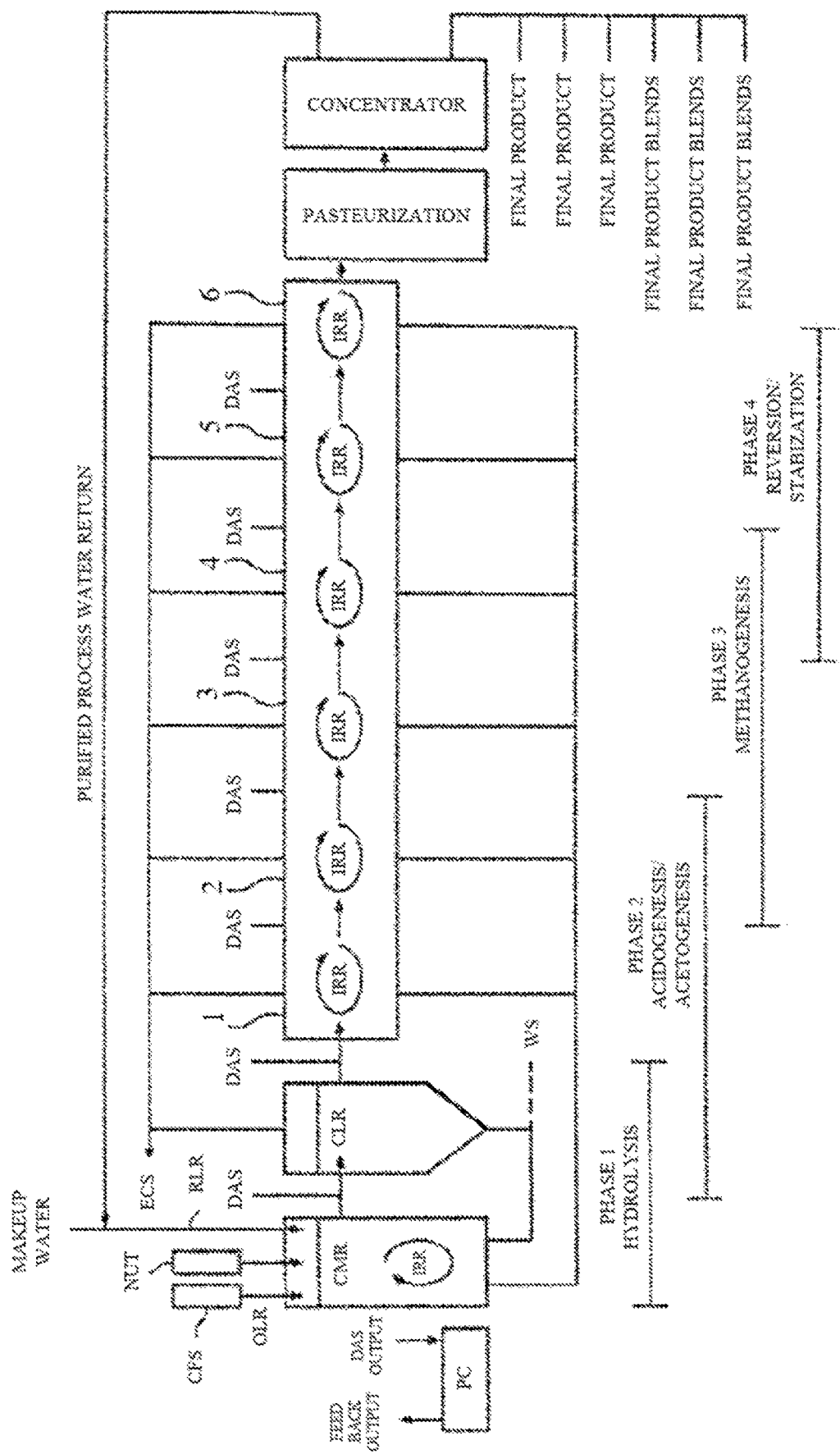
FIG. 6 is a diagram of the preferred embodiment.

Referring to FIG. 6, physical containment system 600 comprises complete mix reactor 601, clarifier 602, and a series of packed bed reactor sections 603, 604, 605, 606, 607, and 608, formed in tube 609. Any number of packed bed reactor sections may be employed. Optionally, pasteurizer 701 may be connected to packed bed reactor section 608 and concentrator 702 may be connected to pasteurizer 701. Concentrator 702 produces final products 660, 661, and 662, and final product blends 663, 664, and 665.

Organic feedstock 656 enters into complete mix reactor 601 at organic load rate 666, nutrient supplements 657 enter complete mix reactor 601, and makeup water 658 enters complete mix reactor 601 at hydraulic load rate 659, forming working fluid 648.

Complete mix reactor 601 circulates working fluid 648 at internal recycle rate 610. In this embodiment, packed bed reactor sections 603, 604, 605, 606, 607, and 608 circulates working fluids 650, 651, 652, 653, 654, and 655 at internal recycle rates 611, 612, 613, 614, 615, and 616, respectively.

In one embodiment, a recirculation system comprising comprises a series of pipes and manifolds extracts a predetermined amount of working fluids 650, 651, 652, 653, 654, and 655 from tube 609, pumps each of working fluids 650, 651, 652, 653, 654, and 655 against the flow direction and then reintroduces working fluids 650, 651, 652, 653, 654, and 655 to tube 609. The internal recycle rate to hydraulic feed rate ratio for each packed bed reactor section is sufficient to maintain each packed bed reactor section as a discrete isolated micro-environment. In this embodiment, the recycle rate ratio of each of packed bed reactor sections 603, 604, 605, 606, 607, and 608 is in a range of approximately 25:1 to 35:1. In another embodiment, the recycle rate ratio for each of packed bed reactor sections 603, 604, 605, 606, 607, and 608 is approximately 30:1.

The temperature of each phase space may vary from 29° C. to 39° C., but the variance across phases should not be greater than 4° C. to preserve the stability within and across physical containment system 600.

In this embodiment, gaseous waste produced in packed bed reactor sections 603, 604, 605, 606, 607, and 608 is vented through a gas-permeable membrane connected to the outside wall of each packed bed reactor section and then discharged through vent pipes 618, 619, 620, 621, 622, and 623 connected to each gas-permeable membrane. Vent pipes 618, 619, 620, 621, 622, and 623 connect to main vent pipe 624. Vent pipe 617 connects to clarifier 602 and main vent pipe 624. Main vent pipe 624 connects to environmental control system 641. Other means known in the art may be employed.

Waste solid outlets 626, 627, 628, 629, 630, and 631 connect to packed reactor sections 603, 604, 605, 606, 607, and 608, respectively. Waste solid outlets 626, 627, 628, 629, 630, and 631 connect to main waste solid outlet 632 to recycle waste solids from each of packed bed reactor sections 603, 604, 605, 606, 607, and 608 to complete mix reactor 601. Recycle connector 625 connects clarifier 602 to complete mix reactor 601 to recycle settled solids. Waste outlet 633 is connects to recycle connector 625 to drain waste solids.

Data acquisition sensor 634 connects to complete mix reactor 601 and clarifier 602, between complete mix reactor 601 and clarifier 602. Data acquisition sensor 634 further connects to process controller 642 at data acquisition sensor input 667. Data acquisition sensor 635 connects to clarifier 602 and packed bed reactor section 603, between clarifier 602 and packed bed reactor section 603 of tube 609. Data acquisition sensor 635 further connects to process controller 642 at data acquisition sensor input 667. Data acquisition sensor 636 connects to tube 609 between packed bed reactor section 603 and packed bed reactor section 604 and to process controller 642 at data acquisition sensor input 667. Data acquisition sensor 637 connects to tube 609 between packed bed reactor section 604 and packed bed reactor section 605 and to process controller 642 at data acquisition sensor input 667. Data acquisition sensor 638 connects to tube 609 between packed bed reactor section 605 and packed bed reactor section 606 and to process controller 642 at data acquisition sensor input 667. Data acquisition sensor 639 connects to tube 609 between packed bed reactor section 606 and packed bed reactor section 607 and to process controller 642 at data acquisition sensor input 667. Data acquisition sensor 640 connects to tube 609 between packed bed reactor section 607 and packed bed reactor section 608 and to process controller 642 at data acquisition sensor input 667. System controls such as pumps, valves, heaters, gas venting systems, timers, and waste solid outlets connect to process controller 642 and, in conjunction with data acquisition sensors 634, 635, 636, 637, 638, 639, and 640, monitor the physical parameters of working fluids 648, 649, 650, 651, 652, 653, 654, and 655 to adjust the system controls through feedback control 643 in the same manner as previously described.

Diverter terminals may be attached to each of packed bed reactor sections 603, 604, 605, 606, 607, and 608 at collection points that may transport working fluids 648, 649, 650, 651, 652, 653, 654, and 655 at any phase for analysis or parallel processing with an alternate processing system.

In this embodiment, the four phases overlap in complete mix reactor 601, clarifier 602, and packed bed reactor sections 603, 604, 605, 606, 607, and 608. The physical locations of each phase along with their respective beginning, peak, and ending are approximate and are not limited to any particular physical vessel or section within a vessel.

First phase 644 begins in complete mix reactor 601, the phase peak approximately occurs in complete mix reactor 601 and clarifier 602, and ends approximately in between clarifier 602 and packed bed reactor section 603 of tube 609.

Second phase 645 begins approximately in complete mix reactor 601 and/or clarifier 602, with the phase peak approximately occurs in clarifier 602, packed bed reactor section 603 or 604, and ends approximately in packed bed reactor section 604 or 605.

Third phase 646 begins approximately in packed bed reactor section 603 or 604, with the phase peak approximately occurs in packed bed reactor section 604, 605, and/or 606, and ends approximately in packed bed reactor section 606 and/or 607.

Fourth phase 647 of this embodiment begins approximately in packed bed reactor section 605 or 606, with the phase peak approximately occurring in packed bed reactor section 606, 607, and/or 608, and ends in packed bed reactor section 608.

Example 4: Optional, Additional Processing

Referring to FIGS. 5 and 6, physical containment systems 500 and 600 may include optional, additional processing steps. In pasteurizer 701, the microbial output product is pumped through a heat exchanger to pre-heat the microbial output product created in the multi-phase bioreactor prior to entry into a boiler system where its temperature is raised to a range of approximately 65° C. to 72° C. and is held at that temperature range for a minimum of approximately one hour. After that time, the microbial output product is cooled by pumping it back through the heat exchanger to efficiently utilize waste and conserve energy.

The microbial output product may also be optionally pumped through a series of filters in concentrator 702. In one embodiment, the filtration process utilizes high pressure membrane filtration to concentrate the microbial output product from the bioreactor by a ratio in a range of approximately 8:1 to 2:1. Other embodiments may use other ratios. This step produces a concentrated final output and purified process water return 703 that connects to makeup water 566 and 658. The water is returned to the hydraulic feed at the beginning of the production process to reduce environmental impact of the multi-phase bioreactor process.

The process may include further steps of freeze drying or blow drying the microbial output product to create customized outputs to that address specific needs in agronomy. This may include using a wettable powder or other water-soluble medium to increase the volume of solids obtained from the drying process applied to the output.

Example 5: Final Microbial Output

When the final microbial output product is produced, TDS and other factors such as clarity and color of product are monitored and compared to expected limits. An aliquot of the final microbial output product may be manually analyzed for chemical and microbial balance. This analysis may also be performed by automated control elements of the system. The computerized process control system may provide information on a display device that indicates when the output is ready for post-production processing.

In this embodiment, the final microbial output product exhibits the following characteristics before the pasteurization and/or concentration step: a pH in a range of approximately 7.5 to 8.8; COD, less than approximately 150 mg/L, more in a range of approximately 90 mg/L to 120 mg/L; and conductivity, which is in a range of approximately 900 µS to 1200 µS. The final microbial output product in this embodiment has a clear amber color and no perceptible scent.

Example 6: Comparison of Microbial Populations in Product Produced by Multiphase Bioreactor System and Legacy System To assess the contribution microbes in the soil additive product to plant growth response, the microbe populations in products generated from the Legacy System (see FIG. 7) ("Legacy products") and the Multiphase Bioreactor System set forth above, hereinafter "Pedigo products" (see FIGS. 5 and 6) were analyzed. Specifically, studies were performed comparing microbial abundance and microbial population diversity in Legacy Products and Pedigo Products.

I. Microbial Abundance

Microbial abundance was determined by plate counts. The total microbial community was determined using biomass analysis of DNA extracted from representative samples.

A. Methods

Plate counts were generated by spreading serial dilutions of product on quarter strength tryptic soy agar (Remel, Lenexa, KY). Plates were incubated at 30° C. for one week before counting colonies with the aid of a dissecting microscope.

Product for molecular analysis was concentrated by centrifugation (7,000×g, 10 min, 4° C.). For Legacy products, 45 ml produced a visible pellet. For Pedigo products, larger volumes—up to 150 ml—were required to produce a pellet. Pellets were transferred to μtubes and community DNA was extracted with the FastDNA™ kit for soil (Qbiogene Inc., Carlsbad, CA) and the bulk DNA was quantified by spectrometry. The contribution of bacterial DNA to this bulk DNA was assessed by quantitative PCR with primers specific for conserved regions of the bacterial 16S rRNA gene as described previously (Hallin et al. 2009 ISME J 3:5970.

B. Results and Discussion

Based on counts of colony forming units (CFU) on standard laboratory media, Pedigo product contains about an order of magnitude less bacteria than Legacy product (×9). This difference was highly significant as determined by ANOVA ($P<0.002$) and consistent for both "raw" (stabilized product) and "AF" (heated and concentrated) product. In terms of CFUs, raw product contained more microbes than AF product. Since generally less than 10% of microbes in mixed microbial communities are detected by these plate counts, we also assessed microbial biomass with molecular techniques.

Product produced by the Pedigo series platform contained less microbes, as assessed by total DNA and qPCR, than that produced by the Legacy platforms. DNA extractions yielded an order of magnitude less bulk DNA from "raw" Pedigo-product (Table 9), where raw represents product that has not been heated and concentrated. Part of this difference in bulk DNA may represent DNA in the feedstock material, which may include DNA from plant material or other sources. To assess bacterial biomass, we applied quantitative PCR (qPCR). This approach measures the total bacterial population and revealed product from the Legacy systems contained 5× more bacteria than product from the Pedigo systems (Table 9). Bacterial biomass, as assessed by qPCR, did not change with heating and concentrating.

TABLE 9

Microbial abundance in Soil Builder-related product produced in Legacy and Pedigo systems.

| System | Process[1] | DNA[2] (ng/ml) | Bacterial Biomass[3] | CFU/ml[4] |
|---|---|---|---|---|
| Legacy | raw | 94 | 4.9 | $1.3 \times 10^8$ |
| Legacy | AF | 103 | 6.9 | $1.4 \times 10^7$ |
| Pedigo | raw | 15 | 1.0 | $1.5 \times 10^7$ |
| Pedigo | AF | 56 | 1.2 | $2.3 \times 10^5$ |

[1]Raw represented stabilized product generated by indicated platform. AF represents heated and concentrated product.
[2]Bulk DNA (see Methods)
[3]Copy 16S × $10^7$ ml$^{-1}$ DNA as assessed by qPCR.
[4]Colony forming units as determined by plating on TSA media.

Bacterial numbers determined by qPCR were in the range ($10^7$ bacteria ml$^{-1}$) determined by plate counts. This was not expected, as generally only a fraction of the bacteria in a microbial community form colonies on standard laboratory conditions. This suggests that qPCR has underestimated the bacterial community. One explanation for this is the primer pair selected does not efficiently amplify all the microbes in the samples analyzed herein. Also, there may be variation in biomass with storage and maturation of systems. Identical samples were not used for DNA and CFU analysis.

The Pedigo product appears to contain significantly less bacteria than Legacy product. This difference did not alter product efficacy, in terms of plant growth response.

II. Microbial Population Diversity

Since the Pedigo product has less microbial biomass than the Legacy product, and systems that contain larger populations generally contain more diverse populations, the Pedigo product was checked to see that this product has a community similar in diversity as the Legacy Product. Three libraries were generated from representative batches generated from each system. Each batch was serially diluted and plated on tryptic soy agar and all the colonies on a plate that yielded between 20 and 30 total colonies were restreaked for isolation. Isolates were classified from these libraries based on fatty acid methyl ester composition using the Sherlock Microbial Identification System following the manufacturer's protocol (MIDI, Inc. Newark, DE).

Pedigo product contained a more diverse bacterial population, as assessed by fatty acid analysis of bacteria isolated from different batches, than Legacy Product. Of the 106 isolates in the libraries, 70 were accurately classified by fatty acid analysis (Table 10). Libraries generated from Pedigo product contained more than 2× the number of rare isolates and nearly 2× the total number of species, than the libraries generated from the Legacy system.

TABLE 10

Diversity of bacteria isolated form Legacy and Pedigo products

| System | Isolates Identified[1] | No Match[2] | Singletons[3] | Species/Library[4] |
|---|---|---|---|---|
| Legacy | 34 | 17 | 10 | 5.3 ± 1.3 |
| Pedigo | 36 | 19 | 25 | 9.3 ± 0.8 |

[1]Isolates were identified by fatty acid analysis with the Sherlock ® system following the manufacturer's protocol (MIDI Inc., Newark, DE).
[2]Isolates not identifiable with Sherlock ® system.
[3]Species that only appeared once in a library.
[4]Average number of species per library. Three libraries were screened from each system.

It will be appreciated by those skilled in the art that modifications can be made to the embodiments disclosed and remain within the inventive concept. Therefore, this disclosure is not limited to the specific embodiments disclosed, but is intended to cover changes within the scope and spirit of the claims.

Various references are cited throughout this specification, each of which is incorporated herein by reference in its entirety.

What is claimed is:

1. A method for processing organic material in a four-phase bioreactor system into a final product containing microbial consortiums and by-products with a chemical oxygen demand (COD) of less than 150 mg/L, wherein movement of said organic material from one phase to the next is hydraulically balanced, and wherein the temperature of said process is maintained between 29° C. and 39° C., the method comprising:
   (a) adding organic feedstock comprising the organic material to said four-phase bioreactor system at a feed rate in a range of 0.001 to about 0.1 pound of organic feedstock per cubic foot of a total working capacity of said four-phase bioreactor system per day;
   (b) passing a working fluid containing said organic material through said four-phase bioreactor system while the working fluid is subjected to four phases comprising:
      (i) a first phase in which said organic material is hydrolyzed to obtain a material of step (i), and in which microbes having methanogen and sulfur-reducing metabolisms, as determined by 16S rRNA gene sequencing, have dominance;
      (ii) a second phase in which said material of step (i) is subject to acidogenesis and acetogenesis to obtain a material of step (ii) which comprises methanogenic precursors hydrogen, carbon dioxide, and acetate;
      (iii) a third phase conducted in a plurality of packed bed reactors to obtain a material of step (iii) wherein each packed bed reactor comprises a fixed media providing a platform for anchoring biofilm and wherein said methanogenic precursors of the material of step (ii) are subjected to methanogenesis and converted to methane, the methane is subjected to methanotrophy, methanotrophs are more abundant than methanogens in the working fluid of said third phase, and at least a portion of the material of step (ii) is subjected to nitrification; and
      (iv) a fourth phase, in which said material of step (iii) is stabilized to produce said final product.

2. The method according to claim 1, wherein said method further comprises pasteurization and/or concentration of the final product.

3. The method according to claim 1, wherein said method further comprises:
   (a) obtaining a set of phase profiles for each phase;
   (b) monitoring a set of physical data from each phase;
   (c) comparing the set of phase profiles from each phase to the set of physical data from each phase;
   (d) deriving a control response to each phase based on the comparison of (c); and
   (e) applying the control response to each phase.

4. The method according to claim 1, wherein said organic material provided to the first phase comprises water and a dry active yeast.

5. The method according to claim 1, wherein said organic material is processed to obtain biostimulants, soil amendments or soil additives, wherein the biostimulants, soil amendments, or soil additives are capable of promoting growth and/or increasing biomass of a plant.

6. The method according to claim 3, wherein the set of physical data is selected from a group consisting of pH level, COD, conductivity and temperature.

7. The method according to claim 1, wherein said organic material is processed between about 5 days and 14 days.

8. The method according to claim 1, wherein the organic material comprises a denitrifying bacterium.

9. The method according to claim 1, wherein said COD in said final product is in the range of approximately 80 mg/L to 150 mg/L.

10. The method according to claim 1, wherein said COD in said final product is in the range of approximately 90 mg/L to 120 mg/L.

11. The method according to claim 1, wherein said hydraulically balanced movement of said organic material from one phase to the next enables said organic material to continuously move in a fixed direction and rate of flow.

12. The method according to claim 1, wherein microbes having nitrification and denitrification metabolisms, as determined by 16S rRNA gene sequencing, have dominance in the second phase.

13. The method according to claim 1, wherein microbes having nitrification and methanotroph metabolisms, as determined by 16S rRNA gene sequencing, have dominance in the third phase space.

14. The method according to claim 1, wherein microbes having nitrification and denitrification metabolisms, a as determined by 16S rRNA gene sequencing, have dominance in the fourth phase space.

* * * * *